US008076078B2

(12) United States Patent
McGinniss et al.

(10) Patent No.: US 8,076,078 B2
(45) Date of Patent: *Dec. 13, 2011

(54) CYSTIC FIBROSIS GENE MUTATIONS

(75) Inventors: Matthew J. McGinniss, San Diego, CA (US); Arlene M. Buller, Rancho Santa Margarita, CA (US); Franklin Quan, Laguna Niguel, CA (US); Mei Peng, Irvine, CA (US); Weimin Sun, Irvine, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/845,102

(22) Filed: Jul. 28, 2010

(65) Prior Publication Data

US 2010/0317017 A1    Dec. 16, 2010

Related U.S. Application Data

(62) Division of application No. 12/015,467, filed on Jan. 16, 2008, now Pat. No. 7,803,548, which is a division of application No. 11/074,903, filed on Mar. 7, 2005.

(60) Provisional application No. 60/550,989, filed on Mar. 5, 2004.

(51) Int. Cl.
*C07H 21/04* (2006.01)
*C12Q 1/68* (2006.01)

(52) U.S. Cl. ...... 435/6.1; 435/6.11; 435/6.12; 435/91.1; 435/91.2; 536/23.1; 536/24.3

(58) Field of Classification Search .................. None
See application file for complete search history.

(56) References Cited

U.S. PATENT DOCUMENTS

| | | | |
|---|---|---|---|
| 4,582,788 A | 4/1986 | Erlich | |
| 4,683,194 A | 7/1987 | Saiki et al. | |
| 4,683,202 A | 7/1987 | Mullis | |
| 4,998,617 A | 3/1991 | Ladd et al. | |
| 5,130,238 A | 7/1992 | Malek et al. | |
| 5,169,766 A | 12/1992 | Schuster et al. | |
| 5,518,900 A | 5/1996 | Nikiforov et al. | |
| 5,846,710 A | 12/1998 | Bajaj | |
| 5,885,775 A | 3/1999 | Haff et al. | |
| 5,888,819 A | 3/1999 | Goelet et al. | |
| 5,955,377 A | 9/1999 | Maul et al. | |
| 5,981,178 A | 11/1999 | Tsui et al. | |
| 6,011,588 A | 1/2000 | Kim | |
| 6,270,963 B1 | 8/2001 | Stevens et al. | |
| 6,288,220 B1 | 9/2001 | Kambara et al. | |
| 6,355,429 B1 | 3/2002 | Nygren et al. | |
| 6,403,320 B1 | 6/2002 | Read et al. | |
| 6,406,844 B1 | 6/2002 | Pirrung et al. | |
| 6,475,724 B1 | 11/2002 | Nguyen et al. | |
| 7,803,548 B1* | 9/2010 | McGinniss et al. | 435/6 |
| 2001/0053519 A1 | 12/2001 | Fodor et al. | |
| 2003/0092019 A1 | 5/2003 | Meyer et al. | |

OTHER PUBLICATIONS

Boat et al, Cystic Fibrosis, The Metabolic Basis of Inherited Disease, 6th ed, pp. 2649-2680, McGraw Hill, NY. (1989).
Claustres et al. (Human Mutation, vol. 26, pp. 143-156, 2000).
Flanigan et al., Rapid Direct Sequence Analysis of the Dystrophin Gene, Am J Hum Genet. Apr;72(4):931-9, (2003).
Genbank Accession M28668, Apr. 1993.
Hirschhorn et al., A comprehensive review of genetic association studies. Genetics in Medicine, 4(2): 45-61, 2002.
Hoogendoorn, B. et al., Genotyping Single Nucleotide Polymorphism by Primer Extension and High Performance Liquid Chromatography, Human Genetics, 104:89-93, (1999).
Ioannidis et al., "Replication validity of genetic association studies" Letter, Nature Genetics, vol. 29, Nov. 2001 306-209.
Jenison et al., Use of a thin film biosensor for rapid visual detection of PCR products in a multiplex format, Biosens Bioelectron. 16(9-12):757-63 (2001).
Kwoh, D. et al., Transcription-based amplification system and detection of amplified human immunodeficiency virus type 1 with a bead-based sandwich hybridization format. Proc. Natl. Acad. Sci. (U.S.A.) 86:1173 (1989).
Landegren, U. et al., A Ligase-Mediated Gene Detection Technique, Science 241:1077-1080, (1988).
McGinniss et al., "Extensive Sequencing of the CFRT gene: lessons learned from the first 157 patient samples" Hum Genet (2005) 118:331-338.
Mullis, K. et al., Specific Enzymatic Amplification of DNA In Vitro: The Polymerase Chain Reaction, Cold Spring Harbor Symp. Quant. Biol. 51:263-273 (1986).
NEB catalog (1998/1999), pp. 121, 284.
Newton, et al., Analysis of any point mututation in DNA. The amplification refractory mutation system (ARMS), Nucleic Acids Res. 17:2503-2516 (1989).
Nickerson et al., Automated DNA diagnostics using an ELISA-based oligonucleotide ligation assay, Proc. Natl. Acad. Sci. U.S.A. 87:8923-8927 (1990).
Nollau et al. (Clinical Chemistry, vol. 43, No. 7, pp. 1114-1128, 1997).
Okayama, et al., Rapid, nonradioactive detection of mutations in the human genome by allele-specific amplification, J. Lab. Clin. Med. 114:105-113 (1989).
Piggee, C. et al. (Capillary Electrophoresis for the Detection of Known Point Mutations by Single-Nucleotide Primer Extension and Laser-Induced Fluorescence Detection) Journal of Chromatography, A 781 p. 367-375 (1997).
Poddar, S.K., Symmetric vs asymmetric PCR and molecular beacon probe in the detection of a target gene of adenovirus, Molec. and Cell. Probes 14:25-32 (2000).
Sarkar, et al., Characterization of Polymerase Chain Reaction Amplification of Specific Allelles, Anal. Biochem. 186:64-68 (1990).

(Continued)

*Primary Examiner* — Jeanine A Goldberg
(74) *Attorney, Agent, or Firm* — Foley & Lardner LLP

(57) ABSTRACT

The present invention provides novel mutations of the CFTR gene related to cystic fibrosis or to conditions associated with cystic fibrosis. Also provided are probes for detecting the mutant sequences. Methods of identifying if an individual has a genotype containing one or more mutations in the CFTR gene are further provided.

11 Claims, 2 Drawing Sheets

OTHER PUBLICATIONS

Strom et al., Extensive sequencing of the cystic fibrosis transmembrane regulator gene: Assay validation and unexpected benefits of developing a comprehensive test. Genetics in Medicine, 5(1):9-14 (2003).

US Notice of Allowance dated May 17, 2010 in related U.S. Appl. No. 12/015,467.

US Office Action dated Feb. 1, 2007 in related U.S. Appl. No. 11/074,903.

US Office Action dated Dec. 31, 2008 in related U.S. Appl. No. 11/074,903.

US Office Action dated Dec. 5, 2007 in related U.S. Appl. No. 11/074,903.

US Office Action dated Mar. 24, 2010 in related U.S. Appl. No. 12/015,467.

US Office Action dated May 16, 2008 in related U.S. Appl. No. 11/074,903.

US Office Action dated Jul. 15, 2009 in related U.S. Appl. No. 12/015,467.

US Office Action dated Aug. 29, 2007 in related U.S. Appl. No. 11/074,903.

Walker, G. T. et al., Isothermal in vitro amplification of DNA by a restriction enzyme/DNA polymerase system, Proc. Natl. Acad. Sci. (U.S.A.) 89:392-396 (1992).

Wu, et al., Allele-specific enzymatic amplification of β-globin genomic DNA for diagnosis of sickle cell anemia, Proc. Natl. Acad. Sci. USA. 86:2757-2760 (1989).

* cited by examiner

FIG. 1
Novel CFTR Mutations

| Mutation Type | Mutation | Nucleotide Change | Location | PCR Primers | CFTR Domain | Clinical Information | Conserved Region |
|---|---|---|---|---|---|---|---|
| missense | S158T | 605G>C | exon 4 | | MSD1 (M2-M3; ICL1) | 4 mo male; abnormal newborn screen, 3 borderline sweat tests(SW) | more conserved than TMs and ECLs in MSDs (Chen et al.) |
| missense | V358I | 1204G>A | exon 7 | q4e1F, q4e1R | MSD1 (between M6-NBD1) | 12 yo male; meconium ileus at birth, respiratory symptoms of CF, SW = 110, 115 | most conserved of MSDs (Chen et al.) |
| deletion | 1198del6 | del TGGGCT (W356+A357) | exon 7 | q7e3F, q7e4R | | | |
| missense | G451V | 1484G>T | exon 9 | g9e9F, g9e11R | NBD1 | 19 yo male; positive SW, CF diagnosis | well conserved (Chen et al.) |
| missense | K481E | 1573 A>G | exon 10 | | NBD1 | 15 yo male: asthma, 2 abnormal SW, no fam history, negative on expanded panel | well conserved (Chen et al.) |
| missense | C491S | 1604 G>C | exon 10 | s10e3F, s10e2R | NBD1 | Patient has no other listed mutations, no known symptoms; sister has P67L (exon 3) and dF508 (exon 10). | well conserved (Chen et al.) |
| deletion & substitution (frameshift) | K503N + frameshift | 1641delA and 1642G>T = 1641 AG>T | exon 10 | s10e3F, s10e2R | NBD1 | 22 yo male; classic CF, pancreatic and pulmonary symptoms, SW = >100 | well conserved (Chen et al.) |
| deletion | 2949del5 | delTACTC | exon 15 | q15e3F, q15e4R | MSD2 (M8-M9; ICL3) | 3 month old female: CF diagnosis | MSD2 is conserved, but less than MSD1 (Chen et al.) |

FIG. 1 (cont'd)
Novel CFTR Mutations

| | | | | | | |
|---|---|---|---|---|---|---|
| missense | H949L | 2978A>T | exon 15 | q15e3F, q15e4R | MSD2 | 12 yo male; lots of sinus involvement, lungs good; atypical CF | MSD2 is conserved, but less than MSD1 (Chen et al.) |
| missense | T1036N | 3239 C>A | exon 17a | q17ae1F, q17ae1R | (M8-M9; ICL3) MSD2 | 15 yo male; classic CF symptoms; negative screen, positive SW | MSD2 is conserved, but less than MSD1 (Chen et al.) |
| missense | F1099L | 3429 C>A | exon 17b | q17be1F, q17be1R | (M10-M11; ICL4) MSD2 | 12 yo male; classic CF symptoms, positive SW | MSD2 is conserved, but less than MSD1 (Chen et al.) |
| | | | | | (M10-M11; ICL4) | | |

SEQUENCE LISTING

<160> NUMBER OF SEQ ID NOS: 46

<210> SEQ ID NO 1
<211> LENGTH: 13
<212> TYPE: DNA
<213> ORGANISM: Artificial Sequence
<220> FEATURE:
<223> OTHER INFORMATION: Description of Artificial Sequence:
      Hypothetical sequence

<400> SEQUENCE: 1
gcggtcccaa aag                                                        13

<210> SEQ ID NO 2
<211> LENGTH: 13
<212> TYPE: DNA
<213> ORGANISM: Artificial Sequence
<220> FEATURE:
<223> OTHER INFORMATION: Description of Artificial Sequence:
      Hypothetical sequence

<400> SEQUENCE: 2
cttttgggac cgc                                                        13

<210> SEQ ID NO 3
<211> LENGTH: 38

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcggtcccaa aagggtcagt tgtaggaagt caccaaag                                    38

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcggtcccaa aagggtcagt cgatacagaa tatatgtgcc                                  40

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcggtcccaa aagggtcagt gaatcattca gtgggtataa gcag                             44

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcggtcccaa aagggtcagt cttcaatgca cctcctccc                                   39

<210> SEQ ID NO 7
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gcggtcccaa aagggtcagt agatacttca atagctcagc c                                41

<210> SEQ ID NO 8
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcggtcccaa aagggtcagt ggtacattac ctgtattttg ttt                              43

<210> SEQ ID NO 9
<211> LENGTH: 40
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 9
gcggtcccaa aagggtcagt gtgaatcgat gtggtgacca                              40

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcggtcccaa aagggtcagt ctggtttagc atgaggcggt                              40

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcggtcccaa aagggtcagt ttggttgtgc tgtggctcct                              40

<210> SEQ ID NO 12
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcggtcccaa aagggtcagt acaatacata caaacatagt gg                           42

<210> SEQ ID NO 13
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcggtcccaa aagggtcagt gaaagtattt attttttctg gaac                         44

<210> SEQ ID NO 14
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcggtcccaa aagggtcagt gtgtgtagaa tgatgtcagc tat                          43

<210> SEQ ID NO 15
<211> LENGTH: 42
<212> TYPE: DNA
<213> ORGANISM: Artificial Sequence
<220> FEATURE:
<223> OTHER INFORMATION: Description of Artificial Sequence: Synthetic
```

```
                                       primer

<400> SEQUENCE: 15
gcggtcccaa aagggtcagt cagattgagc atactaaaag tg                    42

<210> SEQ ID NO 16
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcggtcccaa aagggtcagt tacatgaatg acatttacag ca                    42

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcggtcccaa aagggtcagt aagaactgga tcagggaaga                       40

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcggtcccaa aagggtcagt tccttttgct cacctgtggt                       40

<210> SEQ ID NO 19
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcggtcccaa aagggtcagt ggtcccactt tttattcttt tgc                   43

<210> SEQ ID NO 20
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gcggtcccaa aagggtcagt tggtttctta gtgtttggag ttg                   43

<210> SEQ ID NO 21
<211> LENGTH: 39
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 21
gcggtcccaa aagggtcagt tggatcatgg gccatgtgc                39

<210> SEQ ID NO 22
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gcggtcccaa aagggtcagt actaccttgc ctgctccagt gg            42

<210> SEQ ID NO 23
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gcggtcccaa aagggtcagt aggtagcagc tatttttatg g             41

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gcggtcccaa aagggtcagt taagggagtc ttttgcacaa              40

<210> SEQ ID NO 25
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gcggtcccaa aagggtcagt gcaattttgg atgaccttc                39

<210> SEQ ID NO 26
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcggtcccaa aagggtcagt tagacaggac ttcaaccctc              40

<210> SEQ ID NO 27
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gcggtcccaa aagggtcagt ggtgattatg ggagaactgg                               40

<210> SEQ ID NO 28
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcggtcccaa aagggtcagt atgctttgat gacgcttc                                 38

<210> SEQ ID NO 29
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcggtcccaa aagggtcagt ttcattgaaa agcccgac                                 38

<210> SEQ ID NO 30
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gcggtcccaa aagggtcagt caccttctgt gtattttgct g                            41

<210> SEQ ID NO 31
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gcggtcccaa aagggtcagt aagtattgga caacttgtta gtctc                        45

<210> SEQ ID NO 32
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gcggtcccaa aagggtcagt cgcctttcca gttgtataat tt                           42

<210> SEQ ID NO 33
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tgtaaaacga cggccagtaa agtcttgtgt tgaaattctc agg                          43

<210> SEQ ID NO 34
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
caggaaacag ctatgaccca gctcactacc taatttatga cat                        43

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tgtaaaacga cggccagtct tccattccaa gatccc                                36

<210> SEQ ID NO 36
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
caggaaacag ctatgaccgc aaagttcatt agaactgatc                            40

<210> SEQ ID NO 37
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tgtaaaacga cggccagttg gatcatgggc catgtgc                               37

<210> SEQ ID NO 38
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
caggaaacag ctatgaccaa agagacatgg acaccaaatt aag                        43

<210> SEQ ID NO 39
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tgtaaaacga cggccagtag cagagtacct gaaacagga                             39

<210> SEQ ID NO 40

-continued

```
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
caggaaacag ctatgaccca ttcacagtag cttaccca                              38

<210> SEQ ID NO 41
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tgtaaaacga cggccagtgg ttaagggtgc atgctcttc                             39

<210> SEQ ID NO 42
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
caggaaacag ctatgaccgg ccctattgat ggtggatc                              38

<210> SEQ ID NO 43
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tgtaaaacga cggccagtac actttgtcca ctttgc                                36

<210> SEQ ID NO 44
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
caggaaacag ctatgaccag atgagtatcg cacattc                               37

<210> SEQ ID NO 45
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tgtaaaacga cggccagtat ctattcaaag aatggcac                              38

<210> SEQ ID NO 46
<211> LENGTH: 38
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 46
caggaaacag ctatgaccga taacctatag aatgcagc                              38
```

US 8,076,078 B2

CYSTIC FIBROSIS GENE MUTATIONS

CROSS-REFERENCE TO RELATED PATENT APPLICATIONS

This application is a divisional of U.S. application Ser. No. 12/015,467, filed Jan. 16, 2008 which is a divisional of U.S. application Ser. No. 11/074,903, filed Mar. 7, 2005, which claims the benefit of U.S. Provisional Application No. 60/550,989, filed Mar. 5, 2004, each of which are incorporated herein by reference in its entirety.

FIELD OF THE INVENTION

The present invention relates to novel cystic fibrosis transmembrane regulator (CFTR) gene mutations and for detecting the presence of these mutations in the CFTR gene of individuals.

BACKGROUND OF THE INVENTION

The following description of the background of the invention is provided simply as an aid in understanding the invention and is not admitted to describe or constitute prior art to the invention.

Cystic fibrosis (CF) is the most common severe autosomal recessive genetic disorder in the Caucasian population. It affects approximately 1 in 2,500 live births in North America (Boat et al, The Metabolic Basis of Inherited Disease, 6th ed, pp 2649-2680, McGraw Hill, NY (1989)). Approximately 1 in 25 persons are carriers of the disease. The responsible gene has been localized to a 250,000 base pair genomic sequence present on the long arm of chromosome 7. This sequence encodes a membrane-associated protein called the "cystic fibrosis transmembrane regulator" (or "CFTR"). There are greater than 1000 different mutations in the CFTR gene, having varying frequencies of occurrence in the population, presently reported to the Cystic Fibrosis Genetic Analysis Consortium. These mutations exist in both the coding regions (e.g., ΔF508, a mutation found on about 70% of CF alleles, represents a deletion of a phenylalanine at residue 508) and the non-coding regions (e.g., the 5T, 7T, and 9T mutations correspond to a sequence of 5, 7, or 9 thymidine bases located at the splice branch/acceptor site of intron 8) of the CFTR gene.

The major symptoms of cystic fibrosis include chronic pulmonary disease, pancreatic exocrine insufficiency, and elevated sweat electrolyte levels. The symptoms are consistent with cystic fibrosis being an exocrine disorder. Although recent advances have been made in the analysis of ion transport across the apical membrane of the epithelium of CF patient cells, it is not clear that the abnormal regulation of chloride channels represents the primary defect in the disease.

A variety of CFTR gene mutations are known. The identity of additional mutations will further assist in the diagnosis of cystic fibrosis.

SUMMARY OF THE INVENTION

The inventors have discovered new mutations in the CFTR gene. These mutations, include 605G->C, 1198-1203del/1204G->A (deletes TGGGCT and replaces G with A at position 1204), 1484G->T, 1573A->G, 1604G->C, 1641-1642AG->T, 2949-2953del (deletes TACTC), 2978A->T, 3239C->A, and 3429C->A, are related to the function of the CFTR gene and, therefore, to cystic fibrosis. These mutations are associated with cystic fibrosis or are associated with conditions associated with cystic fibrosis. By "conditions associated with cystic fibrosis" is meant any clinical symptoms that may be found in a cystic fibrosis patient and are due to one or more CF mutations.

Accordingly, in one aspect, the present invention provides a method of determining if a CFTR gene contains one or more mutations selected from the group consisting of 605G->C, 1198-1203del/1204G->A (deletes TGGGCT and replaces G with A at position 1204), 1484G->T, 1573A->G, 1604G->C, 1641-1642AG->T, 2949-2953del (deletes TACTC), 2978A->T, 3239C->A, and 3429C->A, comprising determining if CFTR nucleic acid contains one or more of the mutations.

In another aspect, the present invention provides a method of identifying if an individual has one or more mutations in the CFTR gene comprising determining if nucleic acid from the individual has one more mutations in one or both CFTR genes, the mutations selected from the group consisting of 605G->C, 1198-1203del/1204G->A (deletes TGGGCT and replaces G with A at position 1204), 1484G->T, 1573A->G, 1604G->C, 1641-1642AG->T, 2949-2953del (deletes TACTC), 2978A->T, 3239C->A, and 3429C->A.

In yet another aspect, the present invention provides a method of determining if an individual is predisposed to cystic fibrosis or to a condition associated with cystic fibrosis comprising determining if nucleic acid from the individual has one more mutations in one or both CFTR genes, the mutations selected from the group consisting of 605G->C, 1198-1203del/12040->A (deletes TGGGCT and replaces G with A at position 1204), 14840->T, 1573A->G, 1604G->C, 1641-1642AG->T, 2949-2953del (deletes TACTC), 2978A->T, 3239C->A, and 3429C->A.

In still a further aspect, the present invention provides a method of counseling an individual on the likelihood of having an offspring afflicted with cystic fibrosis or a condition associated with cystic fibrosis, comprising determining if nucleic acid from the individual has one or more mutations in one or both CFTR genes, the mutations selected from the group consisting of 6050->C, 1198-1203del/1204G->A (deletes TGGGCT and replaces G with A at position 1204), 1484G->T, 1573A->G, 16040->C, 1641-1642AG->T, 2949-2953del (deletes TACTC), 2978A->T, 3239C->A, and 3429C->A.

In all of these aspects, the mutations may be 6050->C and 3239C->A. In some embodiments, 1198-1203del (deletes TGGGCT) and the missense 1204G->A may exist separately from the complex allele, 1198-1203del/1204G->A (deletes TGGGCT and replaces G with A at position 1204). In another embodiment, the mutations are selected from the group consisting of 1198-1203del/1204G->A (deletes TGGGCT and replaces G with A at position 1204), 14840->T, 16040->C, 1641-1642AG->T, 2949-2953del (deletes TACTC), 3239C->A, and 3429C->A. In another embodiment the mutations are selected from the group consisting of 6050->C, 1573A->G, and 2978A->T.

In some embodiments, one more mutations are evaluated for both alleles of the CFTR gene in the individual. By this approach the genotype of the individual can be determined at the position of each mutation.

The presence of the mutation in the CFTR gene may be determined by any of a variety of well known methods used to detect single base changes (transitions and/or small deletions/insertions). Thus, genomic DNA may be isolated from the individual and tested for the CF mutations. In another approach, mRNA can be isolated and tested for the CF mutations. Testing may be performed on mRNA or on a cDNA copy.

Genomic DNA or in cDNA may be subject to amplification by the polymerase chain reaction or related methods using primers directed to specific portions of the CFTR gene which contain a mutation to be detected. The sequence of primers suitable for PCR amplification of portions of the CFTR gene in which contain the CF mutations are also provided.

The presence CF mutations can be determined in a nucleic acid by sequencing appropriate portions of the CFTR gene containing the mutations sought to be detected. In another approach, CF mutations that change susceptibility to digestion by one or more endonuclease restriction enzymes may be used to detect the mutations. In another embodiment, the presence of one or more CF mutations can be determined by allele specific amplification. In yet another embodiment, the presence of one or more CF mutations can be determined by primer extension. In yet a further embodiment, the presence of one or more CF mutations can be determined by oligonucleotide ligation. In another embodiment, the presence of one or more CF mutations can be determined by hybridization with a detectably labeled probe containing the mutant CF sequence.

The methods of the invention also may include detection of other CF mutations which are known in the art and which are described herein.

The present invention also provides oligonucleotide probes that are useful for detecting the CF mutations. Accordingly, provided is a substantially purified nucleic acid comprising 8-20 nucleotides fully complementary to a segment of the CFTR gene that is fully complementary to a portion of the CFTR gene and encompasses a mutant CFTR sequence selected from the group consisting of 605G->C, 1204G->A, 1198-1203del (deletes TGGGCT), 1484G->T, 1573A->G, 1604G->C, 1641-1642AG->T, 2949-2953del (deletes TACTC), 2978A->T, 3239C->A, and 3429C->A, or a complementary nucleic acid sequence thereof. In one embodiment, the purified nucleic acid is no more than 50 nucleotides in length. The invention CF mutant probes may be labeled with a detectable label, which may include any of a radioisotope, a dye, a fluorescent molecule, a hapten or a biotin molecule.

In another aspect the present invention provides kits for one of the methods described herein. In various embodiments, the kits contain one or more of the following components in an amount sufficient to perform a method on at least one sample: one or more primers of the present invention, one or more devices for performing the assay, which may include one or more probes that hybridize to a mutant CF nucleic acid sequence, and optionally contain buffers, enzymes, and reagents for performing a method of detecting a genotype of cystic fibrosis in a nucleic acid sample.

BRIEF DESCRIPTION OF THE FIGURES

FIG. 1 is a table showing various CFTR mutations and characterizing information.

DETAILED DESCRIPTION OF THE INVENTION

CF mutations and PCR primer pairs for amplifying segments of the CFTR gene containing the mutation are shown in Table 1.

TABLE 1

CF mutations and associated amplification primers

| CF Mutation | CF Mutation (HGVS Nomenclature)* | Nucleotide Change | Nucleotide Change (HGVS Nomenclature)* | Forward and Reverse PCR Primers |
| --- | --- | --- | --- | --- |
| S158T | p.Ser158Thr | 605G->C | c.473G > C | q4e1F and q4e1R |
| V358I | p.Val358Ile | 1204G->A | c.1072G > A | q7e3F and q7e4R |
| 119del6 | p.Trp356_Ala366del | 1198-1202del (deletes TGGGCT and results in W356 and A357) | c.1066_1071del | q7e3F and q7e4R |
| G451V | p.Gly451Val | 1484G->T | c.1352G > T | q9e9F and q9e11R |
| K481E | p.Lys481Glu | 1573A->G | c.1441A > G | s10e3F and s10e2R |
| C491S | p.Cys491Ser | 1604G->C | c.1472G > C | s10e3F and s10e2R |
| K503N + frameshift | p.Lys503fs | 1641-1642AG->T (deletes 1641A and 1642G and replaces with T) | c.1509_1510delinsT | s10e3F and s10e2R |
| 2949del5 | p.Thr940fs | 2949-2953del (deletes TACTC) | c.2817_2821del | q15e3F and q15e4R |
| H949L | p.His949Leu | 2978A->T | c.2846A > T | q15e3F and q15e4R |
| T1036N | p.Thr1036Asn | 3239C->A | c.3107C > A | q17ae1F and q17ae1R |
| F1099L | p.Phe1099Leu | 3429C->A | c.3297C > A | q17be1F and q17be1R |

*Nomenclature is based on Human Genome Variation Society guidelines as adopted by Cystic Fibrosis Centre at the Hospital for Sick Children in Toronto, Canada and US Cystic Fibrosis Foundation, Bethesda, MD, USA in April 2010

Further information relating to the CF mutations and the CFTR gene are found in FIG. 1. The primers for amplifying segments of the CFTR gene may hybridize to coding or non-coding CFTR sequences under stringent conditions. Preferred primers are those that flank mutant CF sequences. Primers for CF mutations in Table 1 are shown in Table 2.

TABLE 2

Amplification primer sequences for CF mutations

| CF Mutation | Forward and Reverse PCR Primers |
|---|---|
| S158T | q4e1F:<br>(SEQ ID NO: 33)<br>TGTAAAACGACGGCCAGTaaagtcttgtgttgaaattctcagg<br>q4e1R:<br>(SEQ ID NO: 34)<br>CAGGAAACAGCTATGACCCAGCTCACTACCTAATTTATGACAT |
| V358I<br>119del6 | q7e3F:<br>(SEQ ID NO: 35)<br>TGTAAAACGACGGCCAGTcttccattccaagatccc<br>q7e4R:<br>(SEQ ID NO: 36)<br>CAGGAAACAGCTATGACCGCAAAGTTCATTAGAACTGATC |
| G451V | g9e9F:<br>(SEQ ID NO: 37)<br>TGTAAAACGACGGCCAGTtggatcatgggccatgtgc and<br>g9e11R:<br>(SEQ ID NO: 38)<br>CAGGAAACAGCTATGACCAAAGAGACATGGACACCAAATTAAG |
| K481E<br>C491S<br>K503N + frame-shift | s10e3F:<br>(SEQ ID NO: 39)<br>TGTAAAACGACGGCCAGTagcagagtacctgaaacagga<br>s10e2R:<br>(SEQ ID NO: 40)<br>CAGGAAACAGCTATGACCCATTCACAGTAGCTTACCCA |
| 2949del5<br>H949L | q15c3F:<br>(SEQ ID NO: 41)<br>TGTAAAACGACGGCCAGTggttaagggtgcatgctcttc<br>q15e4R:<br>(SEQ ID NO: 42)<br>CAGGAAACAGCTATGACCGGCCCTATTGATGGTGGATC |
| T1036N | q17ae1F:<br>(SEQ ID NO: 43)<br>TGTAAAACGACGGCCAGTacactttgtccactttgc<br>q17ae1R:<br>(SEQ ID NO: 44)<br>CAGGAAACAGCTATGACCAGATGAGTATCGCACATTC |
| F1099L | q17be1F:<br>(SEQ ID NO: 45)<br>TGTAAAACGACGGCCAGTatctattcaaagaatggcac<br>q17be1R:<br>(SEQ ID NO: 46)<br>CAGGAAACAGCTATGACCGATAACCTATAGAATGCAGC |

By "mutations of the CFTR gene" or "mutant CF sequence" is meant one or more CFTR nucleic acid sequences that are associated or correlated with cystic fibrosis. Additional CF mutations are disclosed in Table 3-17 may be correlated with a carrier state, or with a person afflicted with CF. Thus, the nucleic acid may be tested for CF mutations described in any of Tables 1-17. The nucleic acid sequences containing CF mutations are preferably DNA sequences, and are preferably genomic DNA sequences; however, RNA sequences such as mRNA or hnRNA may also contain nucleic acid mutant sequences that are associated with cystic fibrosis.

By "carrier state" is meant a person who contains one CFTR allele that is a mutant CF nucleic acid sequence, but a second allele that is not a mutant CF nucleic acid sequence. CF is an "autosomal recessive" disease, meaning that a mutation produces little or no phenotypic effect when present in a heterozygous condition with a non-disease related allele, but produces a "disease state" when a person is homozygous, i.e., both CFTR alleles are mutant CF nucleic acid sequences.

By "primer" is meant a sequence of nucleic acid, preferably DNA, that hybridizes to a substantially complementary target sequence and is recognized by DNA polymerase to begin DNA replication.

By "substantially complementary" is meant that two sequences hybridize under stringent hybridization conditions. The skilled artisan will understand that substantially complementary sequences need not hybridize along their entire length. In particular, substantially complementary sequences comprise a contiguous sequence of bases that do not hybridize to a target sequence, positioned 3' or 5' to a contiguous sequence of bases that hybridize under stringent hybridization conditions to a target sequence.

By "flanking" is meant that a primer hybridizes to a target nucleic acid adjoining a region of interest sought to be amplified on the target. The skilled artisan will understand that preferred primers are pairs of primers that hybridize 3' from a region of interest, one on each strand of a target double stranded DNA molecule, such that nucleotides may be add to the 3' end of the primer by a suitable DNA polymerase. Primers that flank mutant CF sequences do not actually anneal to the mutant sequence but rather anneal to sequence that adjoins the mutant sequence.

By "isolated" a nucleic acid (e.g., an RNA, DNA or a mixed polymer) is one which is substantially separated from other cellular components which naturally accompany such nucleic acid. The term embraces a nucleic acid sequence which has been removed from its naturally occurring environment, and includes recombinant or cloned DNA isolates, oligonucleotides, and chemically synthesized analogs or analogs biologically synthesized by heterologous systems.

By "substantially pure" a nucleic acid, represents more than 50% of the nucleic acid in a sample. The nucleic acid sample may exist in solution or as a dry preparation.

By "complement" is meant the complementary sequence to a nucleic acid according to standard Watson/Crick pairing rules. For example, a sequence (SEQ ID NO: 1) 5'-GCGGTC-CCAAAAG-3' has the complement (SEQ ID NO: 2) 5'-CTTTTGGGACCGC-3'. A complement sequence can also be a sequence of RNA complementary to the DNA sequence or its complement sequence, and can also be a cDNA.

By "coding sequence" is meant a sequence of a nucleic acid or its complement, or a part thereof, that can be transcribed and/or translated to produce the mRNA for and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the encoding sequence can be deduced therefrom.

By "non-coding sequence" is meant a sequence of a nucleic acid or its complement, or a part thereof, that is not transcribed into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, etc.

Nucleic acid suspected of containing mutant CF sequences are amplified using one or more primers that flank the mutations under conditions such that the primers will amplify CFTR fragments containing the mutations, if present. The oligonucleotide sequences in Table 2 are useful for amplifying segments of the CFTR gene which contain the mutations in Table 1. Nucleic acid from an individual also could be tested for CFTR mutations other than those in Table 1. Such mutations include, for example, any of those listed in Tables 4-18. Primers for these latter CFTR mutations include The method of identifying the presence or absence of mutant CF sequence by amplification can be used to determine whether a subject has a genotype containing one or more nucleotide sequences correlated with cystic fibrosis. The presence of a wildtype or mutant sequence at each predetermined location can be ascertained by the invention methods.

By "amplification" is meant one or more methods known in the art for copying a target nucleic acid, thereby increasing the number of copies of a selected nucleic acid sequence. Amplification may be exponential or linear. A target nucleic acid may be either DNA or RNA. The sequences amplified in this manner form an "amplicon." While the exemplary methods described hereinafter relate to amplification using the polymerase chain reaction ("PCR"), numerous other methods are known in the art for amplification of nucleic acids (e.g., isothermal methods, rolling circle methods, etc.). The skilled artisan will understand that these other methods may be used either in place of, or together with, PCR methods.

The nucleic acid suspected of containing mutant CF sequence may be obtained from a biological sample. By "biological sample" is meant a sample obtained from a biological source. A biological sample can, by way of non-limiting example, consist of or comprise blood, sera, urine, feces, epidermal sample, skin sample, cheek swab, sperm, amniotic fluid, cultured cells, bone marrow sample and/or chorionic villi. Convenient biological samples may be obtained by, for example, scraping cells from the surface of the buccal cavity. The term biological sample includes samples which have been processed to release or otherwise make available a nucleic acid for detection as described herein. For example, a biological sample may include a cDNA that has been obtained by reverse transcription of RNA from cells in a biological sample.

By "subject" is meant a human or any other animal which contains as CFTR gene that can be amplified using the primers and methods described herein. A subject can be a patient, which refers to a human presenting to a medical provider for diagnosis or treatment of a disease. A human includes pre and post natal forms. Particularly preferred subjects are humans being tested for the existence of a CF carrier state or disease state.

By "identifying" with respect to an amplified sample is meant that the presence or absence of a particular nucleic acid amplification product is detected. Numerous methods for detecting the results of a nucleic acid amplification method are known to those of skill in the art.

The present invention provides specific primers that aid in the detection of mutant CF genotype. Such primers enable the amplification of segments of the CFTR gene that are known to contain mutant CF sequence from a nucleic acid containing biological sample. By amplifying specific regions of the CFTR gene, the invention primers facilitate the identification of wildtype or mutant CF sequence at a particular location of the CFTR gene. Primers for amplifying various regions of the CFTR gene include the following: SEQ ID NO: 3, 5'-GCGGTCCCAAAAGGGTCAGTTGTAGGAAGTCACCAAAG-3' (g4e1F), and SEQ ID NO: 4,5'-GCGGTCCCAAAAGGGTCAGTCGATACAGAATATATGTGCC-3' (g4e2R), are preferably used together as forward (F) and reverse (R) primers; SEQ ID NO: 5,5'-GCGGTCCCAAAAGGGTCAGTGAATCATTCAGTGGGTATAAGCAG-3' (g19i2F), and SEQ ID NO: 6, 5'-GCGGTCCCAAAAGGGTCAGTCTTCAATGCACCTCCTCCC-3' (q19i3R), are preferably used together as forward (F) and reverse (R) primers; SEQ ID NO: 7, 5'-GCGGTCCCAAAAGGGTCAGTAGATACTTCAATAGCTCAGCC-3' (g7e1F), and SEQ ID NO: 8,5'-GCGGTCCCAAAAGGGTCAGTGGTACATTACCTGTATTTTGTTT-3' (g7e2R), are preferably used together as forward (F) and reverse (R) primers; SEQ ID NO: 9, 5"-GCGGTCCCAAAAGGGTCAGTGTGAATCGATGTGGTGACCA-3' (s12e1F), and SEQ ID NO: 10, 5'-GCGGTCCCAAAAGGGTCAGTCTGGTTTAGCATGAGGCGGT-3'(s12e1R), are preferably used together as forward (F) and reverse (R) primers; SEQ ID NO: 11, 5'-GCGGTCCCAAAAGGGTCAGTTTGGTTGTGCTGTGGCTCCT-3' (g14be1F), and SEQ ID NO: 12, 5'-GCGGTCCCAAAAGGGTCAGTACAATACATACAAACATAGTGG-3' (g14be2R), are preferably used together as forward (F) and reverse (R) primers; SEQ ID NO: 13, 5'-GCGGTCCCAAAAGGGTCAGTGAAAGTATTTATTTTTTCTGGAAC-3' (q21e1F), and SEQ ID NO: 14 5'-GCGGTCCCAAAAGGGTCAGTGTGTGTAGAATGATGTCAGCTAT-3' (q21e2R), are preferably used together as forward (F) and reverse (R) primers; SEQ ID NO: 15, 5'-GCGGTCCCAAAAGGGTCAGTCAGATTGAGCATACTAAAAGTG-3' (g11 e1F), and SEQ ID NO: 16, 5'-GCGGTCCCAAAAGGGTCAGTTACATGAATGACATTTACAGCA-3' (g11e2R), are preferably used together as forward (F) and reverse (R) primers; SEQ ID NO: 17, 5'-GCGGTCCCAAAAGGGTCAGTAAGAACTGGATCAGGGAAGA-3' (g20e1F), and SEQ ID NO: 18, 5'-GCGGTCCCAAAAGGGTCAGTTCCTTTTGCTCACCTGTGGT-3' (g20e2R), are preferably used as forward (F) and reverse (R) primers; SEQ ID NO: 19, 5'-GCGGTCCCAAAAGGGTCAGTGGTCCCACTTTTTATTCTTTTGC-3' (q3e2F), and SEQ ID NO: 20 5'-GCGGTCCCAAAAGGGTCAGTTGGTTTCTTAGTGTTTGGAGTTG-3' (q3e2R), are preferably used together as forward (F) and reverse (R) primers; SEQ ID NO: 21, 5'-GCGGTCCCAAAAGGGTCAGTTGGATCATGGGCCATGTGC-3' (g9e9F), and SEQ ID NO: 22, 5'-GCGGTCCCAAAAGGGTCAGTACTACCTTGCCTGCTCCAGTGG-3' (g9e9R), are preferably used together as forward (F) and reverse (R) primers; SEQ ID NO: 23, 5'-GCGGTCCCAAAAGGGTCAGTAGGTAGCAGCTATTTTTATGG-3' (g13e2F), and SEQ ID NO: 24, 5'-GCGGTCCCAAAAGGGTCAGTTAAGGGAGTCTTTTGCACAA-3' (g13c2R), are preferably used together as forward (F) and reverse (R) primers; SEQ ID NO: 25 5'-GCGGTCCCAAAAGGGTCAGTGCAATTTTGGATGACCTTC-3' (q16i1F), and SEQ ID NO: 26 5'-GCGGTCCCAAAAGGGTCAGTTAGACAGGACTTCAACCCTC-3' (q16i2R), are preferably used together as forward (F) and reverse (R) primers; SEQ ID NO: 27, 5'-GCGGTCCCAAAAGGGTCAGTGGTGATTATGGGAGAACTGG-3' (q10e10F), and SEQ ID NO: 28, 5'-GCGGTCCCAAAAGGGTCAGTATGCTTTGATGACGCTTC-3' (q10e11R), are preferably used together as forward (F) and reverse (R) primers; SEQ ID NO: 29, 5'-GCGGTCCCAAAAGGGTCAGTTTCATTGAAAAGCCCGAC-3' (q19e12F), and SEQ ID NO: 30, 5'-GCGGTCCCAAAAGGGTCAGTCACCTTCTGTGTATTTTGCTG-3' (q19e13R) are preferably used together as forward (F) and reverse (R) primers; and SEQ ID NO: 31, 5'-GCGGTCCCAAAAGGGTCAGTAAGTATTGGACAACTTGTTAGTCTC-3' (q5e12F), and SEQ ID NO: 32, 5'-GCGGTCCCAAAAGGGTCAGTCGCCTTTCCAGTTGTATAATTT-3' (q5e13R), are preferably used together as forward (F) and reverse (R) primers. These pairs of primers, which may been used in multiplex amplifications, can amplify the regions of the CFTR gene shown in Table 3.

TABLE 3

CFTR Primer Pairs and Amplicon Characteristics

| Forward Primer | Reverse Primer | Exon/Intron | Size |
|---|---|---|---|
| g14be1F (SEQ ID NO. 11) | g14be24 (SEQ ID NO. 12) | 14b/i14b | 149 |
| q5e12F (SEQ ID NO. 31) | q5e13R (SEQ ID NO. 32) | 5/i5 | 165 |
| g20e1F (SEQ ID NO. 17) | g20e2R (SEQ ID NO. 18) | 20 | 194 |
| q16i1F (SEQ ID NO. 25) | q16i2R (SEQ ID NO. 26) | 16/i16 | 200 |
| q10e10F (SEQ ID NO. 27) | q10e11R (SEQ ID NO. 28) | 10 | 204 |
| q21e1F (SEQ ID NO. 13) | q21e2R (SEQ ID NO. 14) | 21 | 215 |
| g11e1F (SEQ ID NO. 15) | g11e2R (SEQ ID NO. 16) | i10/11/i11 | 240 |
| g7e1F (SEQ ID NO. 7) | g7e2R (SEQ ID NO. 8) | 7 | 259 |
| g4e1F (SEQ ID NO. 3) | g4e2R (SEQ ID NO. 4) | 4/i4 | 306 |
| q3e2F (SEQ ID NO. 19) | q3e2R (SEQ ID NO. 20) | 3/i3 | 308 |
| q19e12F (SEQ ID NO. 29) | q1913e2R (SEQ ID NO. 30) | i18/19 | 310 |
| q13e2F (SEQ ID NO. 23) | g13e2R (SEQ ID NO. 24) | 13 | 334 |
| g9e9F (SEQ ID NO. 21) | g9e9R (SEQ ID NO. 22) | i8/9 | 351 |
| g19i2F (SEQ ID NO. 5) | g19i3R (SEQ ID NO. 6) | i19 | 389 |
| s12e1F (SEQ ID NO. 9) | s12e1R (SEQ ID NO. 10) | i11/12/i12 | 465 |

The nucleic acid to be amplified may be from a biological sample such as an organism, cell culture, tissue sample, and the like. The biological sample can be from a subject which includes any eukaryotic organism or animal, preferably fungi, invertebrates, insects, arachnids, fish, amphibians, reptiles, birds, marsupials and mammals. A preferred subject is a human, which may be a patient presenting to a medical provider for diagnosis or treatment of a disease. The biological sample may be obtained from a stage of life such as a fetus, young adult, adult, and the like. Particularly preferred subjects are humans being tested for the existence of a CF carrier state or disease state.

The sample to be analyzed may consist of or comprise blood, sera, urine, feces, epidermal sample, skin sample, cheek swab, sperm, amniotic fluid, cultured cells, bone marrow sample and/or chorionic villi, and the like. A biological sample may be processed to release or otherwise make available a nucleic acid for detection as described herein. Such processing may include steps of nucleic acid manipulation, e.g., preparing a cDNA by reverse transcription of RNA from the biological sample. Thus, the nucleic acid to be amplified by the methods of the invention may be DNA or RNA.

Nucleic acid may be amplified by one or more methods known in the art for copying a target nucleic acid, thereby increasing the number of copies of a selected nucleic acid sequence. Amplification may be exponential or linear. The sequences amplified in this manner form an "amplicon." In a preferred embodiment, the amplification by the is by the polymerase chain reaction ("PCR") (e.g., Mullis, K. et al., Cold Spring Harbor Symp. Quant. Biol. 51:263-273 (1986); Erlich H. et al., European Patent Appln. 50,424; European Patent Appln. 84,796, European Patent Application 258,017, European Patent Appln. 237,362; Mullis, K., European Patent Appln. 201,184; Mullis K. et al., U.S. Pat. No. 4,683,202; Erlich, H., U.S. Pat. No. 4,582,788; and Saiki, R. et al., U.S. Pat. No. 4,683,194). Other known nucleic acid amplification procedures that can be used include, for example, transcription-based amplification systems or isothermal amplification methods (Malek, L. T. et al., U.S. Pat. No. 5,130,238; Davey, C. et al., European Patent Application 329,822; Schuster et al., U.S. Pat. No. 5,169,766; Miller, H. I. et al., PCT appln. WO 89/06700; Kwoh, D. et al., Proc. Natl. Acad. Sci. (U.S.A.) 86:1173 (1989); Gingeras, T. R. et al., PCT Application WO 88/10315; Walker, G. T. et al., Proc. Natl. Acad. Sci. (U.S.A.) 89:392-396 (1992)). Amplification may be performed to with relatively similar levels of each primer of a primer pair to generate an double stranded amplicon. However, asymmetric PCR may be used to amplify predominantly or exclusively a single stranded product as is well known in the art (e.g. Poddar et al. Molec. And Cell. Probes 14:25-32 (2000)). This can be achieved for each pair of primers by reducing the concentration of one primer significantly relative to the other primer of the pair (e.g. 100 fold difference). Amplification by asymmetric PCR is generally linear. One of ordinary skill in the art would know that there are many other useful methods that can be employed to amplify nucleic acid with the invention primers (e.g., isothermal methods, rolling circle methods, etc.), and that such methods may be used either in place of, or together with, PCR methods. Persons of ordinary skill in the art also will readily acknowledge that enzymes and reagents necessary for amplifying nucleic acid sequences through the polymerase chain reaction, and techniques and procedures for performing PCR, are well known. The examples below illustrate a standard protocol for performing PCR and the amplification of nucleic acid sequences that correlate with or are indicative of cystic fibrosis.

In another aspect, the present invention provides methods of detecting a cystic fibrosis genotype in a biological sample. The methods comprise amplifying nucleic acids in a biological sample of the subject and identifying the presence or absence of one or more mutant cystic fibrosis nucleic acid sequences in the amplified nucleic acid. Accordingly, the present invention provides a method of determining the presence or absence of one or more mutant cystic fibrosis nucleic acid sequences in a nucleic acid containing sample, comprising: contacting the sample with reagents suitable for nucleic acid amplification including one or more pairs of nucleic acid primers flanking one or more predetermined nucleic acid sequences that are correlated with cystic fibrosis, amplifying the predetermined nucleic acid sequence(s), if present, to provide an amplified sample; and identifying the presence or absence of mutant or wildtype sequences in the amplified sample.

One may analyze the amplified product for the presence of absence of any of a number of mutant CF sequences that may be present in the sample nucleic acid. As already discussed, numerous mutations in the CFTR gene have been associated with CF carrier and disease states. For example, a three base pair deletion leading to the omission of a phenylalanine residue in the gene product has been determined to correspond to the mutations of the CF gene in approximately 70% of the patients affected by CF. The table below identifies preferred CF sequences and identifies which of the primer pairs of the invention may be used to amplify the sequence.

TABLE 4

CFTR mutations that may be detected in amplified product using as the primer pair SEQ ID NO: 19 and 20.

| Name | Nucleotide change | Exon | Consequence |
|---|---|---|---|
| 297-3C->T | C to T at 297-3 | intron 2 | mRNA splicing defect |
| E56K | G to A at 298 | 3 | Glu to Lys at 56 |
| 300delA | Deletion of A at 300 | 3 | Frameshift |
| W57R | T to C at 301 | 3 | Trp to Arg at 57 |
| W57G | T to G at 301 | 3 | Trp to Gly at 57 |
| W57X(TAG) | G to A at 302 | 3 | Trp to Stop at 57 |
| W57X(TGA) | G to A at 303 | 3 | Trp to Stop at 57 |
| D58N | G to A at 304 | 3 | Asp to Asn at 58 |
| D58G | A to G at 305 | 3 | Asp to Gly at 58 |
| 306insA | Insertion of A at 306 | 3 | Frameshift |
| 306delTAGA | deletion of TAGA from 306 | 3 | Frameshift |
| E60L | G to A at 310 | 3 | Glu to Leu at 60 |
| E60X | G to T at 310 | 3 | Glu to Stop at 60 |
| E60K | G to A at 310 | 3 | Glu to Lys at 60 |
| N66S | A to G at 328 | 3 | Asn to Ser at 66 |
| P67L | C to T at 332 | 3 | Pro to Leu at 67 |
| K68E | A to G at 334 | 3 | Lys to Glu at 68 |
| K68N | A to T at 336 | 3 | Lys to Asn at 68 |
| A72T | G to A at 346 | 3 | Ala to Thr at 72 |
| A72D | C to A at 347 | 3 | Ala to Asp at 72 |
| 347delC | deletion of C at 347 | 3 | Frameshift |
| R74W | C to T at 352 | 3 | Arg to Trp at 74 |
| R74Q | G to A at 353 | 3 | Arg to Gln at 74 |
| R75X | C to T at 355 | 3 | Arg to Stop at 75 |
| R75L | G to T at 356 | 3 | Arg to Leu at 75 |
| 359insT | Insertion of T after 359 | 3 | Frameshift |
| 360delT | deletion of T at 360 | 3 | Frameshift |
| W79R | T to C at 367 | 3 | Trp to Arg at 79 |
| W79X | G to A at 368 | 3 | Trp to Stop at 79 |
| G85E | G to A at 386 | 3 | Gly to Glu at 85 |
| G85V | G to T at 386 | 3 | Gly to Val at 85 |
| F87L | T to C at 391 | 3 | Phe to Leu at 87 |
| 394delTT | deletion of TT from 394 | 3 | frameshift |
| L88S | T to C at 395 | 3 | Leu to Ser at 88 |
| L88X(T->A) | T to A at 395 | 3 | Leu to Stop at 88 |
| L88X(T->G) | T to G at 395 | 3 | Leu to Stop at 88 |
| Y89C | A to G at 398 | 3 | Tyr to Cys at 89 |
| L90S | T to C at 401 | 3 | Leu to Ser at 90 |
| G91R | G to A at 403 | 3 | Gly to Arg at 91 |
| 405 + 1G->A | G to A at 405 + 1 | intron 3 | mRNA splicing defect |
| 405 + 3A->C | A to C at 405 + 3 | intron 3 | mRNA splicing defect |
| 405 + 4A->G | A to G at 405 + 4 | intron 3 | mRNA splicing defect |

TABLE 5

CFTR mutations that may be detected in amplified product using as the primer pair SEQ ID NO: 3 and 4.

| Name | Nucleotide change | Exon | Consequence |
|---|---|---|---|
| A96E | C to A at 419 | 4 | Ala to Glu at 96 |
| Q98X | C to T at 424 | 4 | Gln to Stop at 98 |
| Q98P | A to C at 425 | 4 | Gln to Pro at 98 |
| Q98R | A to G at 425 | 4 | Gln to Arg at 98 |
| P99L | C to T at 428 | 4 | Pro to Leu at 99 |
| L101X | T to G at 434 | 4 | Leu to Stop at 101 |
| 435insA | Insertion of A after 435 | 4 | Frameshift |
| G103X | G to T at 439 | 4 | Gly to Stop at 103 |
| 441delA | deletion of A at 441 and T to A at 486 | 4 | Frameshift |
| 444delA | deletion of A at 444 | 4 | Frameshift |
| I105N | T to A at 446 | 4 | Ile to Asn at 105 |
| 451del8 | deletion of GCTTCCTA from 451 | 4 | Frameshift |
| S108F | C to T at 455 | 4 | Ser to Phe at 108 |
| 457TAT->G | TAT to G at 457 | 4 | Frameshift |
| Y109N | T to A at 457 | 4 | Tyr to Asn at 109 |
| 458delAT | deletion of AT at 458 | 4 | Frameshift |
| Y109C | A to G at 458 | 4 | Tyr to Cys at 109 |
| 460delG | deletion of G at 460 | 4 | Frameshift |
| D110Y | G to T at 460 | 4 | Asp to Tyr at 110 |
| D110H | G to C at 460 | 4 | Asp to His at 110 |
| D110E | C to A at 462 | 4 | Asp to Glu at 110 |
| P111A | C to G at 463 | 4 | Pro to Ala at 111 |
| P111L | C to T at 464 | 4 | Pro to Leu at 111 |
| ΔE115 | 3 bp deletion of 475-477 | 4 | deletion of Glu at 115 |
| E116Q | G to C at 478 | 4 | Glu to Gln at 116 |
| E116K | G to A at 478 | 4 | Glu to Lys at 116 |
| R117C | C to T at 481 | 4 | Arg to Cys at 117 |
| R117P | G to C at 482 | 4 | Arg to Pro at 117 |
| R117L | G to T at 482 | 4 | Arg to Leu at 117 |
| R117H | G to A at 482 | 4 | Arg to His at 117 |
| I119V | A to G at 487 | 4 | Iso to Val at 119 |
| A120T | G to A at 490 | 4 | Ala to Thr at 120 |
| Y122X | T to A at 498 | 4 | Tyr to Stop at 122 |
| I125T | T to C at 506 | 4 | Ile to Thr at 125 |
| G126D | G to A at 509 | 4 | Gly to Asp at 126 |
| L127X | T to G at 512 | 4 | Leu to Stop at 127 |
| 525delT | deletion of T at 525 | 4 | Frameshift |
| 541del4 | deletion of CTCC from 541 | 4 | Frameshift |

TABLE 5-continued

CFTR mutations that may be detected in amplified product using as the primer pair SEQ ID NO: 3 and 4.

| Name | Nucleotide change | Exon | Consequence |
|---|---|---|---|
| 541delC | deletion of C at 541 | 4 | Frameshift |
| L137R | T to G at 542 | 4 | Leu to Arg at 137 |
| L137H | T to A at 542 | 4 | Leu to His at 137 |
| L138ins | insertion of CTA, TAC or ACT at nucleotide 544, 545 or 546 | 4 | insertion of leucine at 138 |
| 546insCTA | Insertion of CTA at 546 | 4 | Frameshift |
| 547insTA | insertion of TA after 547 | 4 | Frameshift |
| H139L | A to T at 548 | 4 | His to Leu at 548 |
| H139R | A to G at 548 | 4 | His to Arg at 139 |
| P140S | C to T at 550 | 4 | Pro to Ser at 140 |
| P140L | C to T at 551 | 4 | Pro to Leu at 140 |
| 552insA | Insertion of A after 552 | 4 | Frameshift |
| A141D | C to A at 554 | 4 | Ala to Asp at 141 |
| 556delA | deletion of A at 556 | 4 | Frameshift |
| 557delT | deletion of T at 557 | 4 | Frameshift |
| 565delC | deletion of C at 565 | 4 | Frameshift |
| H146R | A to G at 569 | 4 | His to Arg at 146 (CBAVD) |
| 574delA | deletion of A at 574 | 4 | Frameshift |
| I148N | T to A at 575 | 4 | Ile to Asn at 148 |
| I148T | T to C at 575 | 4 | Ile to Thr at 148 |
| G149R | G to A at 577 | 4 | Gly to Arg at 149 |
| Q151X | C to T at 583 | 4 | Gln to Stop at 151 |
| M152V | A to G at 586 | 4 | Met to Val at 152 (mutation) |
| M152R | T to G at 587 | 4 | Met to Arg at 152 |
| 591del18 | deletion of 18 bp from 591 | 4 | deletion of 6 amino acids from the CFTR protein |
| A155P | G to C at 595 | 4 | Ala to Pro at 155 |
| S158R | A to C at 604 | 4 | Ser to Arg at 158 |
| 605insT | Insertion of T after 605 | 4 | Frameshift |
| L159X | T to A at 608 | 4 | Leu to Stop at 159 |
| Y161D | T to G at 613 | 4 | Tyr to Asp at 161 |
| Y161N | T to A at 613 | 4 | Tyr to Asn at 161 |
| Y161S | A to C at 614 (together with 612T/A) | 4 | Tyr to Ser at 161 |
| K162E | A to G at 616 | 4 | Lys to Glu at 162 |
| 621G->A | G to A at 621 | 4 | mRNA splicing defect |
| 621+1G->T | G to T at 621 + 1 | intron 4 | mRNA splicing defect |
| 621+2T->C | T to C at 621 + 2 | intron 4 | mRNA splicing defect |
| 621+2T->G | T to G at 621 + 2 | intron 4 | mRNA splicing defect |
| 621+3A->G | A to G at 621 + 3 | intron 4 | mRNA splicing defect |

TABLE 6

CFTR mutations that may be detected in amplified product using as the primer pair SEQ ID NO: 31 and 32.

| Name | Nucleotide_change | Exon | Consequence |
|---|---|---|---|
| 681delC | deletion of C at 681 | 5 | Frameshift |
| N186K | C to A at 690 | 5 | Asn to Lys at 186 |
| N187K | C to A at 693 | 5 | Asn to Lys at 187 |
| ΔD192 | deletion of TGA or GAT from 706 or 707 | 5 | deletion of Asp at 192 |
| D192N | G to A at 706 | 5 | Asp to Asn at 192 |
| D192G | A to G at 707 | 5 | Asp to Gly at 192 |
| E193K | G to A at 709 | 5 | Glu to Lys at 193 |
| E193X | G to T at 709 | 5 | Glu to Stop at 193 |
| 711+1G->T | G to T at 711 + 1 | intron 5 | mRNA splicing defect |
| 711+3A->G | A to G at 711 + 3 | intron 5 | mRNA splicing defect |
| 711+3A->C | A to C at 711 + 3 | intron 5 | mRNA splicing defect |
| 711+3A->T | A to T at 711 + 3 | intron 5 | mRNA splicing defect |
| 711+5G->A | G to A at 711 + 5 | intron 5 | mRNA splicing defect |
| 711+34A->G | A to G at 711 + 34 | intron 5 | mRNA splicing defect |

TABLE 7

CFTR mutations that may be detected in amplified product using as the primer pair SEQ ID NO: 7 and 8.

| Name | Nucleotide_change | Exon | Consequence |
|---|---|---|---|
| ΔF311 | deletion of 3 bp between 1059 and 1069 | 7 | deletion of Phe310, 311 or 312 |
| F311L | C to G at 1065 | 7 | Phe to Leu at 311 |
| G314R | G to C at 1072 | 7 | Gly to Arg at 314 |
| G314E | G to A at 1073 | 7 | Gly to Glu at 314 |
| G314V | G to T at 1073 | 7 | Gly to Val at 324 |

TABLE 7-continued

CFTR mutations that may be detected in amplified product using as the primer pair SEQ ID NO: 7 and 8.

| Name | Nucleotide_change | Exon | Consequence |
|---|---|---|---|
| F316L | T to G at 1077 | 7 | Phe to Leu at 316 |
| 1078delT | deletion of T at 1078 | 7 | Frameshift |
| V317A | T to C at 1082 | 7 | Val to Ala at 317 |
| L320V | T to G at 1090 | 7 | Leu to Val at 320 CAVD |
| L320X | T to A at 1091 | 7 | Leu to Stop at 320 |
| L320F | A to T at 1092 | 7 | Leu to Phe at 320 |
| V322A | T to C at 1097 | 7 | Val to Ala at 322 |
| 1112delT | deletion of T at 1112 | 7 | Frameshift |
| L327R | T to G at 1112 | 7 | Leu to Arg at 327 |
| 1119delA | deletion of A at 1119 | 7 | Frameshift |
| G330X | G to T at 1120 | 7 | Gly to Stop at 330 |
| R334W | C to T at 1132 | 7 | Arg to Trp at 334 |
| R334Q | G to A at 1133 | 7 | Arg to Gln at 334 |
| R334L | G to T at 1133 | 7 | Arg to Leu at 334 |
| 1138insG | Insertion of G after 1138 | 7 | Frameshift |
| I336K | T to A at 1139 | 7 | Ile to Lys at 336 |
| T338I | C to T at 1145 | 7 | Thr to Ile at 338 |
| 1150delA | deletion of A at 1150 | 7 | Frameshift |
| 1154insTC | insertion of TC after 1154 | 7 | Frameshift |
| 1161insG | Insertion of G after 1161 | 7 | Frameshift |
| 1161delC | deletion of C at 1161 | 7 | Frameshift |
| L346P | T to C at 1169 | 7 | Leu to Pro at 346 |
| R347C | C to T at 1171 | 7 | Arg to Cys at 347 |
| R347H | G to A at 1172 | 7 | Arg to His at 347 |
| R347L | G to T at 1172 | 7 | Arg to Leu at 347 |
| R347P | G to C at 1172 | 7 | Arg to Pro at 347 |
| M348K | T to A at 1175 | 7 | Met to Lys at 348 |
| A349V | C to T at 1178 | 7 | Ala to Val at 349 |
| R352W | C to T at 1186 | 7 | Arg to Trp at 352 |
| R352Q | G to A at 1187 | 7 | Arg to Gln at 352 |
| Q353X | C to T at 1189 | 7 | Gln to Stp at 353 |
| Q353H | A to C at 1191 | 7 | Gln to His at 353 |
| 1199delG | deletion of G at 1199 | 7 | Frameshift |
| W356X | G to A at 1200 | 7 | Trp to Stop at 356 |
| Q359K/T360K | C to A at 1207 and C to A at 1211 | 7 | Glu to Lys at 359 and Thr to Lys at 360 |
| Q359R | A to G at 1208 | 7 | Gln to Arg at 359 |
| 1213delT | deletion of T at 1213 | 7 | Frameshift |
| W361R(T->C) | T to C at 1213 | 7 | Trp to Arg at 361 |
| W361R(T->A) | T to A at 1213 | 7 | Trp to Arg at 361 |
| 1215delG | deletion of G at 1215 | 7 | Frameshift |
| 1221delCT | deletion of CT from 1221 | 7 | Frameshift |
| S364P | T to C at 1222 | 7 | Ser to Pro at 364 |
| L365P | T to C at 1226 | 7 | Leu to Pro at 365 |

TABLE 8

CFTR mutations that may be detected in amplified product using as the primer pair SEQ ID NO: 21 and 22.

| Name | Nucleotide_change | Exon | Consequence |
|---|---|---|---|
| 1342-11TTT->G | TTT to G at 1342-11 | intron 8 | mRNA splicing defect |
| 1342-2delAG | deletion of AG from 1342-2 | intron 8 | Frameshift |
| 1342-2A->C | A to C at 1342-2 | intron 8 | mRNA splicing defect |
| 1342-1G->C | G to C at 1342-1 | intron 8 | mRNA splicing defect |
| E407V | A to T at 1352 | 9 | Glu to Val at 407 |
| 1366delG | deletion of G at 1366 | 9 | Frameshift |
| 1367delC | deletion of C at 1367 | 9 | Frameshift |
| 1367del5 | deletion of CAAAA at 1367 | 9 | Frameshift |
| Q414X | C to T at 1372 | 9 | Gln to Stop at 414 |
| N418S | A to G at 1385 | 9 | Asn to Ser at 418 |
| G424S | G to A at 1402 | 9 | Gly to Ser at 424 |
| S434X | C to G at 1433 | 9 | Ser to Stop at 434 |
| D443Y | G to T at 1459 | 9 | Asp to Tyr at 443 |
| 1460delAT | deletion of AT from 1460 | 9 | Frameshift |
| 1461ins4 | insertion of AGAT after 1461 | 9 | Frameshift |
| I444S | T to G at 1463 | 9 | Ile to Ser at 444 |
| 1471delA | deletion of A at 1471 | 9 | Frameshift |
| Q452P | A to C at 1487 | 9 | Gln to Pro at 452 |
| ΔL453 | deletion of 3 bp between 1488 and 1494 | 9 | deletion of Leu at 452 or 454 |

TABLE 8-continued

CFTR mutations that may be detected in amplified product using as the primer pair SEQ ID NO: 21 and 22.

| Name | Nucleotide_change | Exon | Consequence |
|---|---|---|---|
| A455E | C to A at 1496 | 9 | Ala to Glu at 455 |
| V456F | G to T at 1498 | 9 | Val to Phe at 456 |

TABLE 9

CFTR mutations that may be detected in amplified product using as the primer pair SEQ ID NO: 27 and 28.

| Name | Nucleotide_change | Exon | Consequence |
|---|---|---|---|
| G480C | G to T at 1570 | 10 | Gly to Cys at 480 |
| G480D | G to A at 1570 | 10 | Gly to Asp at 480 |
| G480S | G to A at 1570 | 10 | Gly to Ser at 480 |
| 1571delG | deletion of G at 1571 | 10 | Frameshift |
| 1576insT | Insertion of T at 1576 | 10 | Frameshift |
| H484Y | C to T at 1582 | 10 | His to Tyr at 484 (CBAVD) |
| H484R | A to G at 1583 | 10 | His to Arg at 484 |
| S485C | A to T at 1585 | 10 | Ser to Cys at 485 |
| G486X | G to T at 1588 | 10 | Glu to Stop at 486 |
| S489X | C to A at 1598 | 10 | Ser to Stop at 489 |
| 1601delTC | deletion of TC from 1601 or CT from 1602 | 10 | Frameshift |
| C491R | T to C at 1603 | 10 | Cys to Arg at 491 |
| S492F | C to T at 1607 | 10 | Ser to Phe at 492 |
| Q493X | C to T at 1609 | 10 | Gln to Stop at 493 |
| 1609delCA | deletion of CA from 1609 | 10 | Frameshift |
| Q493R | A to G at 1610 | 10 | Gln to Arg at 493 |
| 1612delTT | deletion of TT from 1612 | 10 | Frameshift |
| W496X | G to A at 1619 | 10 | Trp to Stop at 496 |
| P499A | C to G at 1627 | 10 | Pro to Ala at 499 (CBAVD) |
| T501A | A to G at 1633 | 10 | Thr to Ala at 501 |
| I502T | T to C at 1637 | 10 | Ile to Thr at 502 |
| I502N | T to A at 1637 | 10 | Ile to Asn at 502 |
| E504X | G to T at 1642 | 10 | Glu to Stop at 504 |
| E504Q | G to C at 1642 | 10 | Glu to Gln at 504 |
| I506L | A to C at 1648 | 10 | Ile to Leu at 506 |
| ΔI507 | deletion of 3 bp between 1648 and 1653 | 10 | deletion of Ile506 or Ile507 |
| I506S | T to G at 1649 | 10 | Ile to Ser at 506 |
| I506T | T to C at 1649 | 10 | Ile to Thr at 506 |
| ΔF508 | deletion of 3 bp between 1652 and 1655 | 10 | deletion of Phe at 508 |
| F508S | T to C at 1655 | 10 | Phe to Ser at 508 |
| D513G | A to G at 1670 | 10 | Asp to Gly at 513 (CBAVD) |
| 1677delTA | deletion of TA from 1677 | 10 | frameshift |
| Y517C | A to G at 1682 | 10 | Tyr to Cys at 517 |

TABLE 10

CFTR mutations that may be detected in amplified product using as the primer pair SEQ ID NO: 15 and 16.

| Name | Nucleotide_change | Exon | Consequence |
|---|---|---|---|
| 1716-1G->A | G to A at 1716-1 | intron 10 | mRNA splicing defect |
| 1717-8G->A | G to A at 1717-8 | intron 10 | mRNA splicing defect |
| 1717-3T->G | T to G at 1717-3 | intron 10 | mRNA splicing defect |
| 1717-2A->G | A to G at 1717-2 | intron 10 | mRNA splicing defect |
| 1717-1G->A | G to A at 1717-1 | intron 10 | mRNA splicing defect |
| D529H | G to C at 1717 | 11 | Asp to His at 529 |
| 1717-9T->A | T to A at 1717-9 | intron 10 | mRNA splicing mutation |
| A534E | C to A at 1733 | 11 | Ala to Glu at 534 |
| 1742delAC | deletion of AC from 1742 | 11 | Frameshift |
| I539T | T to C at 1748 | 11 | Ile to Thr at 539 |
| 1749insTA | Insertion of TA at 1749 | 11 | frameshift resulting in premature termination at 540 |
| G542X | G to T at 1756 | 11 | Gly to Stop at 542 |
| G544S | G to A at 1762 | 11 | Gly to Ser at 544 |
| G544V | G to T at 1763 | 11 | Gly to Val at 544 (CBAVD) |
| 1774delCT | deletion of CT from 1774 | 11 | Frameshift |

TABLE 10-continued

CFTR mutations that may be detected in amplified product using as the primer pair SEQ ID NO: 15 and 16.

| Name | Nucleotide_change | Exon | Consequence |
|---|---|---|---|
| S549R(A->C) | A to C at 1777 | 11 | Ser to Arg at 549 |
| S549I | G to T at 1778 | 11 | Ser to Ile at 549 |
| S549N | G to A at 1778 | 11 | Ser to Asn at 549 |
| S549R(T->G) | T to G at 1779 | 11 | Ser to Arg at 549 |
| G550X | G to T at 1780 | 11 | Gly to Stop at 550 |
| G550R | G to A at 1780 | 11 | Gly to Arg at 550 |
| 1782delA | deletion of A at 1782 | 11 | Frameshift |
| G551S | G to A at 1783 | 11 | Gly to Ser at 551 |
| 1784delG | deletion of G at 1784 | 11 | Frameshift |
| G551D | G to A at 1784 | 11 | Gly to Asp at 551 |
| Q552X | C to T at 1786 | 11 | Gln to Stop at 552 |
| Q552K | C to A at 1786 | 11 | Gln to Lys |
| 1787delA | deletion of A at position 1787 or 1788 | 11 | frameshift, stop codon at 558 |
| R553G | C to G at 1789 | 11 | Arg to Gly at 553 |
| R553X | C to T at 1789 | 11 | Arg to Stop at 553 |
| R553Q | G to A at 1790 | 11 | Arg to Gln at 553 (associated with ΔF508); |
| R555G | A to G at 1795 | 11 | Arg to Gly at 555 |
| I556V | A to G at 1798 | 11 | Ile to Val at 556 |
| 1802delC | deletion of C at 1802 | 11 | Frameshift |
| L558S | T to C at 1805 | 11 | Leu to Ser at 558 |
| 1806delA | deletion of A at 1806 | 11 | Frameshift |
| A559T | G to A at 1807 | 11 | Ala to Thr at 559 |
| A559E | C to A at 1808 | 11 | Ala to Glu at 559 |
| R560T | G to C at 1811 | 11 | Arg to Thr at 560; mRNA splicing defect |
| R560K | G to A at 1811 | 11 | Arg to Lys at 560 |
| 1811+1G->C | G to C at 1811 + 1 | intron 11 | mRNA splicing defect |
| 1811+1.6kbA->G | A to G at 1811 + 1.2kb | intron 11 | creation of splice donor site |
| 1811+18G->A | G to A at 1811 + 18 | intron 11 | mRNA splicing defect |

TABLE 11

CFTR mutations that may be detected in amplified product using as the primer pair SEQ ID NO: 9 and 10.

| Name | Nucleotide change | Exon | Consequence |
|---|---|---|---|
| 1812-1G->A | G to A at 1812-1 | intron 11 | mRNA splicing defect |
| R560S | A to C at 1812 | 12 | Arg to Ser at 560 |
| 1813insC | Insertion of C after 1813 (or 1814) | 12 | Frameshift |
| A561E | C to A at 1814 | 12 | Ala to Glu at 561 |
| V562I | G to A at 1816 | 12 | Val to Ile at 562 |
| V562L | G to C at 1816 | 12 | Val to Leu at 562 |
| Y563D | T to G at 1819 | 12 | Tyr to Asp at 563 |
| Y563N | T to A at 1819 | 12 | Tyr to Asn at 563 |
| Y563C | A to G at 1821 | 12 | Tyr to Cys at 563 |
| 1833delT | deletion of T at 1833 | 12 | Frameshift |
| L568X | T to A at 1835 | 12 | Leu to Stop at 568 |
| L568F | G to T at 1836 | 12 | Leu to Phe at 568 (CBAVD) |
| Y569D | T to G at 1837 | 12 | Tyr to Asp at 569 |
| Y569H | T to C at 1837 | 12 | Tyr to His at 569 |
| Y569C | A to G at 1838 | 12 | Tyr to Cys at 569 |
| V569X | T to A at 1839 | 12 | Tyr to Stop at 569 |
| L571S | T to C at 1844 | 12 | Leu to Ser at 571 |
| 1845delAG/1846delGA | deletion of AG at 1845 or GA at 1846 | 12 | Frameshift |
| D572N | G to A at 1846 | 12 | Asp to Asn at 572 |
| P574H | C to A at 1853 | 12 | Pro to His at 574 |
| G576X | G to T at 1858 | 12 | Gly to Stop at 576 |
| G576A | G to C at 1859 | 12 | Gly to Ala at 576 (CAVD) |
| Y577F | A to T at 1862 | 12 | Tyr to Phe at 577 |
| D579Y | G to T at 1867 | 12 | Asp to Tyr at 579 |
| D579G | A to G at 1868 | 12 | Asp to Gly at 579 |
| D579A | A to C at 1868 | 12 | Asp to Ala at 579 |
| 1870delG | deletion of T between 1871 | 12 | Frameshift |
| 1874insT | Insertion of T between 1871 and 1874 | 12 | Frameshift |
| T582R | C to G at 1877 | 12 | Thr to Arg at 582 |
| T582I | C to T at 1877 | 12 | Thr to Ile at 582 |

TABLE 11-continued

CFTR mutations that may be detected in amplified product using as the primer pair SEQ ID NO: 9 and 10.

| Name | Nucleotide change | Exon | Consequence |
|---|---|---|---|
| E585X | G to T at 1885 | 12 | Glu to Stop at 585 |
| S589N | G to A at 1898 | 12 | Ser to Asn at 589 (mRNA splicing defect) |
| S589I | G to T at 1898 | 12 | Ser to Ile at 589 (splicing) |
| 1898+1G->A | G to A at 1898 + 1 | intron 12 | mRNA splicing defect |
| 1898+1G->C | G to C at 1898 + 1 | intron 12 | mRNA splicing defect |
| 1898+1G->T | G to T at 1898 + 1 | intron 12 | mRNA splicing defect |
| 1898+3A->G | A to G at 1898 + 3 | intron 12 | mRNA splicing defect |
| 1898+3A->C | A to C at 1898 + 3 | intron 12 | mRNA splicing defect |
| 1898+5G->A | G to A at 1898 + 5 | intron 12 | mRNA splicing defect |
| 1898+5G->T | G to T at 1898 + 5 | intron 12 | mRNA splicing defect |
| 1898+73T->G | T to G at 1898 + 73 | intron 12 | mRNA splicing defect |

TABLE 12

CFTR mutations that may be detected in amplified product using as the primer pair SEQ ID NO: 23 and 24.

| Name | Nucleotide_change | Exon | Consequence |
|---|---|---|---|
| 1918delGC | deletion of GC from 1918 | 13 | Frameshift |
| 1924del7 | deletion of 7 bp (AAACTA) from 1924 | 13 | Frameshift |
| R600G | A to G at 1930 | 13 | Arg to Gly at 600 |
| I601F | A to T at 1933 | 13 | Ile to Phe at 601 |
| V603F | G to T at 1939 | 13 | Val to Phe at 603 |
| T604I | C to T at 1943 | 13 | Thr to Ile at 604 |
| 1949del84 | deletion of 84 bp from 1949 | 13 | deletion of 28 a.a. (Met607 to Gln634) |
| H609R | A to G at 1958 | 13 | His to Arg at 609 |
| L610S | T to C at 1961 | 13 | Leu to Ser at 610 |
| A613T | G to A at 1969 | 13 | Ala to Thr at 613 |
| D614Y | G to T at 1972 | 13 | Asp to Tyr 614 |
| D614G | A to G at 1973 | 13 | Asp to Gly at 614 |
| I618T | T to C at 1985 | 13 | Ile to Thr at 618 |
| L619S | T to C at 1988 | 13 | Leu to Ser at 619 |
| H620P | A to C at 1991 | 13 | His to Pro at 620 |
| H620Q | T to G at 1992 | 13 | His to Gln at 620 |
| G622D | G to A at 1997 | 13 | Gly to Asp at 622 (oligospermia) |
| G628R(G->A) | G to A at 2014 | 13 | Gly to Arg at 628 |
| G628R(G->C) | G to C at 2014 | 13 | Gly to Arg at 628 |
| L633P | T to C at 2030 | 13 | Leu to Pro at 633 |
| Q634X | T to A at 2032 | 13 | Gln to Stop at 634 |
| L636P | T to C at 2039 | 13 | Leu to Pro at 636 |
| Q637X | C to T at 2041 | 13 | Gln to Stop at 637 |
| 2043delG | deletion of G at 2043 | 13 | Frameshift |
| 2051delTT | deletion of TT from 2051 | 13 | Frameshift |
| 2055del9->A | deletion of 9 bp CTCAAAACT to A at 2055 | 13 | Frameshift |
| D648V | A to T at 2075 | 13 | Asp to Val at 648 |
| D651N | G to A at 2083 | 13 | Asp to Asn at 651 |
| E656X | T to G at 2098 | 13 | Glu to Stop at 656 |
| 2108delA | deletion of A at 2108 | 13 | Frameshift |
| 2109del9->A | deletion of 9bp from 2109 and insertion of A | 13 | Frameshift |
| 2113delA | deletion of A at 2113 | 13 | Frameshift |
| 2116delCTAA | deletion of CTAA at 2116 | 13 | Frameshift |
| 2118del4 | deletion of AACT from 2118 | 13 | Frameshift |
| E664X | G to T at 2122 | 13 | Glu to Stop at 664 |
| T665S | A to T at 2125 | 13 | Thr to Ser at 665 |
| 2141insA | Insertion of A after 2141 | 13 | Frameshift |
| 2143delT | deletion of T at 2143 | 13 | Frameshift |
| E672del | deletion of 3 bp between 2145-2148 | 13 | deletion of Glu at 672 |
| G673X | G to T at 2149 | 13 | Gly to Stop at 673 |
| W679X | G to A at 2168 | 13 | Trp to stop at 679 |
| 2176insC | Insertion of C after 2176 | 13 | Frameshift |
| K683R | A to G at 2180 | 13 | Lys to Arg at 683 |
| 2183AA->G | A to G at 2183 and deletion of A at 2184 | 13 | Frameshift |
| 2183delAA | deletion of AA at 2183 | 13 | Frameshift |

TABLE 12-continued

CFTR mutations that may be detected in amplified product using as the primer pair SEQ ID NO: 23 and 24.

| Name | Nucleotide_change | Exon | Consequence |
|---|---|---|---|
| 2184delA | deletion of A at 2184 | 13 | frameshift |
| 2184insG | inserion of G after 2184 | 13 | Frameshift |
| 2184insA | Insertion of A after 2184 | 13 | Frameshift |
| 2185insC | Insertion of C at 2185 | 13 | Frameshift |
| Q685X | C to T at 2185 | 13 | Gln to Stop at 685 |
| E692X | G to T at 2206 | 13 | Glu to Stop at 692 |
| F693L(CTT) | T to C at 2209 | 13 | Phe to Leu at 693 |
| F693L(TTG) | T to G at 2211 | 13 | Phe to Leu at 693 |
| 2215insG | Insertion of G at 2215 | 13 | Frameshift |
| K698R | A to G 2225 | 13 | Lys to Arg at 698 |
| R709X | C to T at 2257 | 13 | Arg to Stop at 709 |
| K710X | A to T at 2260 | 13 | Lys to Stop at 710 |
| K716X | AA to GT at 2277 and 2278 | 13 | Lys to Stop at 716 |
| L719X | T to A at 2288 | 13 | Leu to Stop at 719 |
| Q720X | C to T at 2290 | 13 | Gln to stop codon at 720 |
| E725K | G to A at 2305 | 13 | Glu to Lys at 725 |
| 2307insA | Insertion of A after 2307 | 13 | Frameshift |
| E730X | G to T at 2320 | 13 | Glu to Stop at 730 |
| L732X | T to G at 2327 | 13 | Leu to Stop at 732 |
| 2335delA | deletion of A at 2335 | 13 | Frameshift |
| R735K | G to A at 2336 | 13 | Arg to Lys at 735 |
| 2347delG | deletion of G at 2347 | 13 | Frameshift |
| 2372del8 | deletion of 8 bp from 2372 | 13 | Frameshift |
| P750L | C to T at 2381 | 13 | Pro to Leu at 750 |
| V754M | G to A at 2392 | 13 | Val to Met at 754 |
| T760M | C to T at 2411 | 13 | Thr to Met at 760 |
| R764X | C to T at 2422 | 13 | Arg to Stop at 764 |
| 2423delG | deletion of G at 2423 | 13 | Frameshift |
| R766M | G to T at 2429 | 13 | Arg to Met at 766 |
| 2456delAC | deletion of AC at 2456 | 13 | Frameshift |
| S776X | C to G at 2459 | 13 | Ser to Stop at 776 |

TABLE 13

CFTR mutations that may be detected in amplified product using as the primer pair SEQ ID NO: 11 and 12.

| Name | Nucleotide_change | Exon | Consequence |
|---|---|---|---|
| T908N | C to A at 2788 | 14b | Thr to Asn at 908 |
| 2789+2insA | insertion of A after 2789 + 2 | intron 14b | mRNA splicing defect (CAVD) |
| 2789+3delG | deletion of G at 2789 + 3 | intron 14b | mRNA splicing defect |
| 2789+5G->A | G to A at 2789 + 5 | intron 14b | mRNA splicing defect |

TABLE 14

CFTR mutations that may be detected in amplified product using as the primer pair SEQ ID NO: 25 and 26.

| Name | Nucleotide_change | Exon | Consequence |
|---|---|---|---|
| 3100insA | Insertion of A after 3100 | 16 | Frameshift |
| I991V | A to G at 3103 | 16 | Ile to Val at 991 |
| D993Y | G to T at 3109 | 16 | Asp to Tyr at 993 |
| F994C | T to G at 3113 | 16 | Phe to Cys at 994 |
| 3120G->A | G to A at 3120 | 16 | mRNA splicing defect |
| 3120+1G->A | G to A at 3120 + 1 | intron 16 | mRNA splicing defect |

TABLE 15

CFTR mutations that may be detected in amplified product using as the primer pair SEQ ID NO: 29 and 30.

| Name | Nucleotide_change | Exon | Consequence |
|---|---|---|---|
| 3601-20T->C | T to C at 3601-20 | intron 18 | mRNA splicing mutant |
| 3601-17T->C | T to C at 3601-17 | intron 18 | mRNA splicing defect |
| 3601-2A->G | A to G at 3601-2 | intron 18 | mRNA splicing defect |
| R1158X | C to T at 3604 | 19 | Arg to Stop at 1158 |
| S1159P | T to C at 3607 | 19 | Ser to Pro at 115p |
| S1159F | C to T at 3608 | 19 | Ser to Phe at 1159 |
| R1162X | C to T at 3616 | 19 | Arg to Stop at 1162 |
| 3622insT | Insertion of T after 3622 | 19 | Frameshift |
| D1168G | A to G at 3635 | 19 | Asp to Gly at 1168 |
| 3659delC | deletion of C at 3659 | 19 | Frameshift |
| K1177X | A to T at 3661 | 19 | Lys to Stp at 3661 (premature termination) |
| K1177R | A to G at 3662 | 19 | Lys to Arg at 1177 |
| 3662delA | deletion of A at 3662 | 19 | Frameshift |

TABLE 15-continued

CFTR mutations that may be detected in amplified product using as the primer pair SEQ ID NO: 29 and 30.

| Name | Nucleotide_change | Exon | Consequence |
|---|---|---|---|
| 3667del4 | deletion of 4 bp from 3667 | 19 | Frameshift |
| 3667ins4 | insertion of TCAA after 3667 | 19 | Frameshift |
| 3670delA | deletion of A at 3670 | 19 | Frameshift |
| Y1182X | C to G at 3678 | 19 | Tyr to Stop at 1182 |
| Q1186X | C to T at 3688 | 19 | Gln to Stop codon at 1186 |
| 3696G/A | G to A at 3696 | 19 | No change to Ser at 1188 |
| V1190P | T to A at 3701 | 19 | Val to Pro at 1190 |
| S1196T | C or Q at 3719 | 19 | Ser-Top at 1196 |
| S1196X | C to G at 3719 | 19 | Ser to Stop at 1196 |
| 3724delG | deletion of G at 3724 | 19 | Frameshift |
| 3732delA | deletion of A at 3732 and A to G at 3730 | 19 | frameshift and Lys to Glu at 1200 |
| 3737delA | deletion of A at 3737 | 19 | Frameshift |
| W1204X | G to A at 3743 | 19 | Trp to Stop at 1204 |
| S1206X | C to G at 3749 | 19 | Ser to Stop at 1206 |
| 3750delAG | deletion of AG from 3750 | 19 | Frameshift |
| 3755delG | deletion of G between 3751 and 3755 | 19 | Frameshift |
| M1210I | G to A at 3762 | 19 | Met to Ile at 1210 |
| V1212I | G to A at 3766 | 19 | Val to Ile at 1212 |

TABLE 16

CFTR mutations that may be detected in amplified product using as the primer pair SEQ ID NO: 5 and 6.

| Name | Nucleotide_change | Exon | Consequence |
|---|---|---|---|
| 3849+10kbC->T | C to T in a 6.2 kb EcoRI fragment 10 kb from 19 | intron 19 | creation of splice acceptor site |

TABLE 17

CFTR mutations that may be detected in amplified product using as the primer pair SEQ ID NO: 17 and 18.

| Name | Nucleotide_change | Exon | Consequence |
|---|---|---|---|
| T1252P | A to C at 3886 | 20 | Thr to Pro at 1252 |
| L1254X | T to G at 3893 | 20 | Leu to Stop at 1254 |
| S1255P | T to C at 3895 | 20 | Ser to Pro at 1255 |
| S1255L | C to T at 3896 | 20 | Ser to Leu at 1255 |
| S1255X | C to A at 3896 and A to G at 3739 in exon 19 | 20 | Ser to Stop at 1255 and Ile to Val at 1203 |
| 3898insC | Insertion of C after 3898 | 20 | Frameshift |
| F1257L | T to G at 3903 | 20 | Phe to Leu at 1257 |
| 3905insT | Insertion of T after 3905 | 20 | Frameshift |
| 3906insG | Insertion of G after 3906 | 20 | Frameshift |
| ΔL1260 | deletion of ACT from either 3909 or 3912 | 20 | deletion of Leu at 1260 or 1261 |
| 3922del10->C | deletion of 10 bp from 3922 and replacement with 3921 | 20 | deletion of Glu1264 to Glu1266 |
| I1269N | T to A at 3938 | 20 | Ile to Asn at 1269 |
| D1270N | G to A at 3940 | 20 | Asp to Asn at 1270 |
| 3944delGT | deletion of GT from 3944 | 20 | Frameshift |
| W1274X | G to A at 3954 | 20 | Trp to Stop at 1274 |
| Q1281X | C to T at 3973 | 20 | Gln to Stop at 1281 |
| W1282R | T to C at 3976 | 20 | Trp to Arg at 1282 |
| W1282G | T to G at 3976 | 20 | Trp to Gly at 1282 |
| W1282X | G to A at 3978 | 20 | Trp to Stop at 1282 |
| W1282C | G to T at 3978 | 20 | Trp to Cys at 1282 |
| R1283M | G to T at 3980 | 20 | Arg to Met at 1283 |
| R1283K | G to A at 3980 | 20 | Arg to Lys at 1283 |
| F1286S | T to C at 3989 | 20 | Phe to Ser at 1286 |

TABLE 18

CFTR mutations that may be detected in amplified product using as the primer pair SEQ ID NO: 13 and 14.

| Name | Nucleotide_change | Exon | Consequence |
|---|---|---|---|
| T1299I | C to T at 4028 | 21 | Thr to Ile at 1299 |
| F1300L | T to C at 4030 | 21 | Phe to Leu at 1300 |
| N1303H | A to C at 4039 | 21 | Asn to His at 1303 |
| N1303I | A to T at 4040 | 21 | Asn to Ile at 1303 |
| 4040delA | deletion of A at 4040 | 21 | Frameshift |
| N1303K | C to G at 4041 | 21 | Asn to Lys at 1303 |
| D1305E | T to A at 4047 | 21 | Asp to Glu at 1305 |
| 4048insCC | insertion of CC after 4048 | 21 | Frameshift |
| Y1307X | T to A at 4053 | 21 | Tyr to Stop at 1307 |
| E1308X | G to T at 4054 | 21 | Glu to Stop at 1308 |

CF mutations including those known under symbols: 2789+5G>A; 711+1G>T; W1282X; 3120+1G>A; d1507; dF508; (F508C, 1507V, 1506V); N1303K; G542X, G551D, R553X, R560T, 1717-1G>A: R334W, R347P, 1078delT; R117H, 1148T, 621+1G>T; G85E; R1162X, 3659delC; 2184delA; A455E, (5T, 7T, 9T); 3849+10 kbC>T; and 1898+ 1G>A, are described in U.S. patent application Ser. No. 396, 894, tiled Apr. 22, 1989, U.S. patent application Ser. No. 399,945, filed Aug. 29, 1989, U.S. patent application Ser. No. 401,609 filed Aug. 31, 1989. and U.S. Pat. Nos. 6,001,588 and 5,981,178, which are hereby incorporated by reference in their entirety. Any and all of these mutations can be detected using nucleic acid amplified with the invention primers as described herein.

CF mutations in the amplified nucleic acid may be identified in any of a variety of ways well known to those of ordinary skill in the art. For example, if an amplification product is of a characteristic size, the product may be detected by examination of an electrophoretic gel for a band at a precise location. In another embodiment, probe molecules that hybridize to the mutant or wildtype CF sequences can be used for detecting such sequences in the amplified product by solution phase or, more preferably, solid phase hybridization. Solid phase hybridization can be achieved, for example, by attaching the CF probes to a microchip. Probes for detecting CF mutant sequences are well known in the art. See Wall et al. "A 31-mutation assay for cystic fibrosis testing in the clinical molecular diagnostics laboratory," Human Mutation, 1995; 5(4):333-8, which specifies probes for CF mutations ΔF508 (exon 1), G542X (exon 11), G551D (exon 11), R117H (exon 4), W1282X (exon 20), N1303K (exon 21), 3905insT (exon 20), 3849+10 Kb (intron 19), G85E (exon 3), R334W (exon 7), A455E (exon 9), 1898+1 (exon 12), 2184delA (exon 13), 711+1 (exon 5), 2789+5 (exon 14b), Y1092x exon 17b), ΔI507 (exon 10), S549R(T-G) (exon 11), 621+1 (exon 4), R1162X (exon 19), 1717-1 (exon 11), 3659delC (exon 19), R560T (exon 11), 3849+4(A-G) (exon 19), Y122X (exon 4), R553X (exon 11), R347P (exon 7), R347H (exon 7), Q493X (exon 10), V520F (exon 10), and S549N (exon 11).

CF probes for detecting mutations as described herein may be attached to a solid phase in the form of an array as is well known in the art (see, U.S. Pat. Nos. 6,403,320 and 6,406, 844). For example, the full complement of 24 probes for CF mutations with additional control probes (30 in total) can be conjugated to a silicon chip essentially as described by Jenison et al Biosens Bioelectron, 16(9-12):757-63 (2001) (see also U.S. Pat. Nos. 6,355,429 and 5,955,377). Amplicons that hybridized to particular probes on the chip can be identified by transformation into molecular thin films. This can be achieved by contacting the chip with an anti-biotin antibody or streptavidin conjugated to an enzyme such as horseradish peroxidase. Following binding of the antibody (or streptavidin)-enzyme conjugate to the chip, and washing away excess unbound conjugate, a substrate can be added such as tetramethylbenzidine (TMB) {3,3',5,5'Tetramethylbenzidine} to achieve localized deposition (at the site of bound antibody) of a chemical precipitate as a thin film on the surface of the chip. Other enzyme/substrate systems that can be used are well known in the art and include, for example, the enzyme alkaline phosphatase and 5-bromo-4-chloro-3-indolyl phosphate as the substrate. The presence of deposited substrate on the chip at the locations in the array where probes are attached can be read by an optical scanner. U.S. Pat. Nos. 6,355,429 and 5,955,377, which are hereby incorporated by reference in their entirety including all charts and drawings, describe preferred devices for performing the methods of the present invention and their preparation, and describes methods for using them.

The binding of amplified nucleic acid to the probes on the solid phase following hybridization may be measured by methods well known in the art including, for example, optical detection methods described in U.S. Pat. No. 6,355,429. In preferred embodiments, an array platform (see, e.g., U.S. Pat. No. 6,288,220) can be used to perform the methods of the present invention, so that multiple mutant DNA sequences can be screened simultaneously. The array is preferably made of silicon, but can be other substances such as glass, metals, or other suitable material, to which one or more capture probes are attached. In preferred embodiments, at least one capture probe for each possible amplified product is attached to an array. Preferably an array contains 10, more preferably 20, even more preferably 30, and most preferably at least 60 different capture probes covalently attached to the array, each capture probe hybridizing to a different CF mutant sequence. Nucleic acid probes useful as positive and negative controls also may be included on the solid phase or used as controls for solution phase hybridization.

Another approach, variously referred to as PCR amplification of specific allele (PASA) (Sarkar et al., 1990 Anal. Biochem. 186:64-68), allele-specific amplification (ASA) (Okayama, et al., 1989 J. Lab. Clin. Med. 114:105-113), allele-specific PCR (ASPCR) (Wu, et al. 1989 Proc. Natl. Acad. Sci. USA. 86:2757-2760), and amplification-refractory mutation system (ARMS) (Newton, et al., 1989 Nucleic Acids Res. 17:2503-2516). The method is applicable for single base substitutions as well as micro deletions/insertions. In general, two complementary reactions are used. One contains a primer specific for the normal allele and the other reaction contains a primer for the mutant allele (both have a common 2nd primer). One PCR primer perfectly matches one allelic variant of the target, but is mismatched to the other. The mismatch is located at/near the 3' end of the primer leading to preferential amplification of the perfectly matched allele. Genotyping is based on whether there is amplification in one or in both reactions. A hand in the normal reaction only indicates a normal allele. A hand in the mutant reaction only indicates a mutant allele. Bands in both reactions indicate a heterozygote. As used herein, this approach will be referred to as "allele specific amplification."

In yet another approach, restriction fragment length polymorphism (RFLP), which refers to the digestion pattern of various restriction enzymes applied to DNA. RFLP analysis can be applied to PCR amplified DNA to identify CF mutations as disclosed herein.

In still another approach, wildtype or mutant CF sequence in amplified DNA may be detected by direct sequence analysis of the amplified products. A variety of methods can be used for direct sequence analysis as is well known in the art.

See, e.g., The PCR Technique: DNA Sequencing (eds. James Ellingboe and Ulf Gyllensten) Biotechniques Press, 1992; see also "SCAIP" (single condition amplification/internal primer) sequencing, by Flanigan et al. Am J Hum Genet. 2003 April; 72(4):931-9. Epub 2003 Mar. 11. Direct sequencing of CF mutations is also described in Strom et al., 2003 *Genetics in Medicine* 5(1):9-14.

In yet another approach for detecting wildtype or mutant CF sequences in amplified DNA is single nucleotide primer extension or "SNuPE." SNuPE can be performed as described in U.S. Pat. No. 5,888,819 to Goelet et al., U.S. Pat. No. 5,846,710 to Bajaj, Piggee, C. et al. Journal of Chromatography A 781 (1997), p. 367-375 ("Capillary Electrophoresis for the Detection of Known Point Mutations by Single-Nucleotide Primer Extension and Laser-Induced Fluorescence Detection"); Hoogendoorn, B. et al., Human Genetics (1999) 104:89-93, ("Genotyping Single Nucleotide Polymorphism by Primer Extension and High Performance Liquid Chromatography"); and U.S. Pat. No. 5,885,775 to Haff et al. (analysis of single nucleotide polymorphism analysis by mass spectrometry). In SNuPE, one may use as primers such as those specified in Table 17.

Another method for detecting CF mutations include the Luminex xMAP system which has been adapted for cystic fibrosis mutation detection by TM Bioscience and is sold commercially as a universal bead array (Tag-It™)

Still another approach for detecting wildtype or mutant CF sequences in amplified DNA is oligonucleotide ligation assay or "OLA" or "OL". The OLA uses two oligonucleotides which are designed to be capable of hybridizing to abutting sequences of a single strand of a target molecules. One of the oligonucleotides is biotinylated, and the other is detectably labeled. If the precise complementary sequence is found in a target molecule, the oligonucleotides will hybridize such that their termini abut, and create a ligation substrate that can be captured and detected. See e.g., Nickerson et al. (1990) Proc. Natl. Acad. Sci. U.S.A. 87:8923-8927, Landegren, U. et al. (1988) Science 241:1077-1080 and U.S. Pat. No. 4,998,617.

These above approaches for detecting wildtype or mutant CF sequence in the amplified nucleic acid is not meant to be limiting, and those of skill in the art will understand that numerous methods are known for determining the presence or absence of a particular nucleic acid amplification product.

In another aspect the present invention provides kits for one of the methods described herein. The kit optionally contain buffers, enzymes, and reagents for amplifying the CFTR nucleic acid via primer-directed amplification. The kit also may include one or more devices for detecting the presence or absence of particular mutant CF sequences in the amplified nucleic acid. Such devices may include one or more probes that hybridize to a mutant CF nucleic acid sequence, which may be attached to a bio-chip device, such as any of those described in U.S. Pat. No. 6,355,429. The bio-chip device optionally has at least one capture probe attached to a surface on the bio-chip that hybridizes to a mutant CF sequence. In preferred embodiments the bio-chip contains multiple probes, and most preferably contains at least one probe for a mutant CF sequence which, if present, would be amplified by a set of flanking primers. For example, if five pairs of flanking primers are used for amplification, the device would contain at least one CF mutant probe for each amplified product, or at least five probes. The kit also preferably contains instructions for using the components of the kit.

The following examples serve to illustrate the present invention. These examples are in no way intended to limit the scope of the invention

EXAMPLES

Example 1

Sample Collection and Preparation

Whole Blood: 5 cc of whole blood is collected in a lavender-top (EDTA) tube or yellow-top (ACD) tube. Green-top (Na Heparin) tubes are acceptable but less desirable. DNA is extracted from blood. 100 ng or more DNA is prepared in TE or sterile water.

Amniotic Fluid: 10-15 cc of Amniotic Fluid is collected in a sterile plastic container.

Cultured Cells: Two T-25 culture flasks with 80-100% confluent growth may be used.

Chorionic 10-20 mg of Chorionic Villi are collected in a sterile container. 2-3 mL of sterile saline or tissue culture medium is added.

Transport: Whole Blood, Amniotic Fluid, Cultured Cells and Chorionic Villi can be shipped at room temperature (18°-26° C.). Amniotic Fluid, Cultured Cells or Chorionic Villi preferably is used without refrigeration or freezing. Whole Blood and Extracted DNA can be shipped at 2°-10° C.

Storage: Whole Blood, Amniotic Fluid and Extracted DNA are stored at 2°-10° C., Cultured Cells and Chorionic Villi are stored at room temperature (18°-26° C.).

Stability: Whole Blood is generally stable for 8 days at room temperature (18°-26° C.) or 8 days refrigerated at 2°-10° C. Amniotic Fluid, Cultured Cells, and Chorionic Villi are generally processed to obtain DNA within 24 hours of receipt. Extracted DNA is stable for at least 1 year at 2°-10° C.

Example 2

Amplification from DNA

Polymerase chain reaction (PCR) primer pairs were designed using the CFTR gene sequences in EMBL/Genbank (Accession Nos. M55106-M55131). Each PCR primer for the 32 separate PCR reactions contains either an M13 forward linker sequence or an M13 reverse linker sequence as appropriate to allow universal sequence reaction priming. Individual PCR reactions are performed in 96-well microtiter plates under the same conditions for each amplicon. Subsequently, the PCR products are purified with the Millipore Montage™ $PCR_{96}$ Cleanup kit (Millipore, Bedford, Mass.) on a Beckman BioMek 2,000 biorobot. Further details are provided in Strom et al., 2003 *Genetics in Medicine* 5(1):9-14.

In general, individual amplifications are prepared in a volume of 13.5 which is added to the 96 well microtiter plates. Each amplification volume contained 2 µl of the nucleic acid sample (generally 10-100 ng of DNA), 11.5 µl of PCR-Enzyme Mix (PCR-Enzyme mix stock is prepared with 11.3 µl master mix, 0.25 µl $MgCl_2$ (from 25 mM stock), and 0.2 µl of FasStar Taq (source for last two reagents was Roche Applied science, Cat. No. 2 032 937). Master mix contained primers, Roche PCR buffer with $MgCl_2$, Roche GC rich solution (cat. No. 2 032 937), bovine serum albumin (BSA) (New England BioLabs, Cat no. B9001B), and NTPs (Amersham Biosciences, Cat no. 27-2032-01).

The final concentration in the PCR for $MgCl_2$ was 2.859 mM, for BSA is 0.725 µg, and for each dNTP is 0.362 mM. Primer final concentrations varied from about 0.29 µM to about 0.036 µM PCR is conducted using the following temperature profile: step 1: 96° C. for 15 minutes; step 2: 94° C. for 15 seconds;

step 3: decrease at 0.5° C./second to 56° C.; step 4: 56° C. for 20 seconds; step 5: increase at 0.3° C./second to 72° C., step 6: 72° C. for 30 seconds; step 7: increase 0.5° C. up to 94° C.; step 8: repeat steps 2 to 7 thirty three times; step 9: 72° C. for 5 minutes; step 10: 4° C. hold (to stop the reaction).

Example 3

Detection of CF Mutations

The purified PCR products are diluted to approximately 10 ng/μL and cycle sequencing reactions are performed with an ABI Prism Big Dye™ Terminator v3.0 cycle sequencing reaction kit (Applied Biosystems, Foster City, Calif.) according to the manufacturer's protocol. The DNA primers used for the sequencing reaction are M13 forward and reverse primers as appropriate. Big Dye™ Terminator reaction products are purified by the Millipore Montage™ Seq$_{96}$ Sequencing Reaction Cleanup kit on a biorobot and analyzed on an ABI Prism 3100 Genetic Analyzer. Sequences obtained are examined for the presence of mutations by using ABI SeqScape v1.1 software. Both strands of DNA are sequenced.

All PCR reactions, purifications, and cycle sequencing reactions are performed in 96-well microtiter plates using biorobots to avoid errors introduced by manual setups. Loading of samples onto the capillary sequencer is also automated. One plate is sufficient to perform the entire sequencing reaction for a single patient. Theoretically, if all reactions were successful, the entire sequences for a single patient could be obtained in 24-48 hours after receipt of blood. In practice, however, one or more reactions must be repeated because of frequent polymorphisms in intron 8 and 6a and failed reactions.

The contents of the articles, patents, and patent applications, and all other documents and electronically available information mentioned or cited herein, are hereby incorporated by reference in their entirety to the same extent as if each individual publication was specifically and individually indicated to be incorporated by reference.

Applicants reserve the right to physically incorporate into this application any and all materials and information from any such articles, patents, patent applications, or other physical and electronic documents.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

We claim:

1. A method of determining the cystic fibrosis status of a human comprising:
   (a) determining the presence or absence of the c.3297C>A mutation, which results in F1099L/p.Phe1099Leu, in both alleles of the cystic fibrosis transmembrane regulatory (CFTR) gene in a nucleic acid sample obtained from the human, and
   (b) identifying the human
      (i) as having cystic fibrosis or being predisposed to cystic fibrosis when the human is homozygous for the c.3297C>A mutation in the CFTR gene, or
      (ii) as being a cystic fibrosis carrier when the human is heterozygous for the c.3297C>A mutation in the CFTR gene, or
      (iii) as having no predisposition or carrier status caused by the c.1352G>T mutation when the c.3297C>A mutation is absent from both alleles of the CFTR gene.

2. A method of determining if a human is predisposed to cystic fibrosis comprising:
   (a) determining the presence or absence of the c.3297C>A mutation, which results in F1099L/p.Phe1099Leu. in both alleles of the cystic fibrosis transmembrane regulatory (CFTR) gene in a nucleic acid sample obtained from the human, and
   (b) identifying said human
      (i) as being predisposed to cystic fibrosis when the human is homozygous for the c.3297C>A mutation in the CFTR gene, or
      (ii) as having no predisposition to cystic fibrosis when the human is heterozygous for the c.3297C>A mutation in the CFTR gene or the c.3297C>A mutation is absent from both alleles of the CFTR gene.

3. A method of identifying a human as having an increased likelihood of having an offspring afflicted with cystic fibrosis, comprising
   (a) determining the presence or absence of the c.3297C>A mutation, which results in F1099L/p.Phe1099Leu, in both alleles of the CFTR gene in a nucleic acid sample obtained from the human, and
   (b) identifying said human as having an increased likelihood of having an offspring afflicted with cystic fibrosis when said c.3297C>A mutation is present in at least one allele.

4. The method of any one of claims 1-3 wherein genomic DNA is tested for the presence of said mutation.

5. The method of any one of claims 1-3 wherein a cDNA copy of the CFTR coding sequence is tested for the presence of said mutation.

6. The method of any one of claims 1-3 wherein the presence of said mutation is determined by nucleic acid sequencing.

7. The method of any one of claims 1-3 wherein the presence of said mutation is determined by restriction fragment length polymorphism analysis following treatment of CFTR gene sequence with at least one endonuclease restriction enzyme.

8. The method of any one of claims 1-3 wherein the presence of said mutation is determined by allele specific amplification.

9. The method of any one of claims 1-3 wherein the presence of said mutation is determined by primer extension.

10. The method of any one of claims 1-3 wherein the presence of said mutation is determined by oligonucleotide ligation.

11. The method of any one of claims 1-3 wherein the presence of said mutation is determined by hybridization with a detectably labeled probe.

* * * * *